US 6,569,463 B2

(12) United States Patent
Patel et al.

(10) Patent No.: US 6,569,463 B2
(45) Date of Patent: *May 27, 2003

(54) SOLID CARRIERS FOR IMPROVED DELIVERY OF HYDROPHOBIC ACTIVE INGREDIENTS IN PHARMACEUTICAL COMPOSITIONS

(75) Inventors: Mahesh V. Patel, Salt Lake City, UT (US); Feng-Jing Chen, Salt Lake City, UT (US)

(73) Assignee: Lipocine, Inc., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/800,593

(22) Filed: Mar. 6, 2001

(65) Prior Publication Data

US 2003/0064097 A1 Apr. 3, 2003

Related U.S. Application Data

(62) Division of application No. 09/447,690, filed on Nov. 23, 1999, now Pat. No. 6,248,363.

(51) Int. Cl.⁷ .............................. A61K 9/16; A61K 9/28; A61K 9/32; A61K 9/52; A61K 9/56; A61K 9/58

(52) U.S. Cl. ..................... 424/497; 424/422; 424/427; 424/430; 424/433; 424/434; 424/435; 424/436; 424/441; 424/451; 424/457; 424/463; 424/464; 424/465; 424/466; 424/470; 424/474; 424/476; 424/482; 424/490; 424/489; 424/498; 514/773; 514/784; 514/785; 514/786; 514/779

(58) Field of Search .......................... 424/422, 433, 424/436, 435, 440, 451, 452, 464, 465, 482, 489, 490, 480, 463, 470, 497, 498, 476, 427, 430, 434, 441, 466, 474

(56) References Cited

U.S. PATENT DOCUMENTS

| 4,717,569 A | 1/1988 | Harrison et al. | |
|---|---|---|---|
| 4,849,227 A | 7/1989 | Cho | |
| 4,867,984 A | 9/1989 | Patel | |
| 5,023,108 A | 6/1991 | Bagaria et al. | |
| 5,340,589 A | 8/1994 | Stetsko et al. | |
| 5,380,535 A | 1/1995 | Geyer et al. | |
| 5,571,533 A | * 11/1996 | Santus et al. | 424/469 |
| 5,573,783 A | 11/1996 | Desieno et al. | |
| 5,624,687 A | 4/1997 | Yano et al. | |
| 5,633,015 A | 5/1997 | Gilis et al. | |
| 5,645,856 A | * 7/1997 | Lacy et al. | 424/455 |
| 5,811,120 A | 9/1998 | Gibson et al. | |
| 5,846,971 A | 12/1998 | Sangekar et al. | |
| 5,891,469 A | 4/1999 | Amselem | |
| 6,248,363 B1 | * 6/2001 | Patel et al. | 424/497 |

* cited by examiner

Primary Examiner—James M. Spear
(74) Attorney, Agent, or Firm—Dianne E. Reed; Reed & Eberle LLP

(57) ABSTRACT

The present invention provides solid pharmaceutical compositions for improved delivery of a wide variety of pharmaceutical active ingredients contained therein or separately administered. In one embodiment, the solid pharmaceutical composition includes a solid carrier, the solid carrier including a substrate and an encapsulation coat on the substrate. The encapsulation coat can include different combinations of pharmaceutical active ingredients, hydrophilic surfactant, lipophilic surfactants and triglycerides. In another embodiment, the solid pharmaceutical composition includes a solid carrier, the solid carrier being formed of different combinations of pharmaceutical active ingredients, hydrophilic surfactants, lipophilic surfactants and triglycerides. The compositions of the present invention can be used for improved delivery of hydrophilic or hydrophobic pharmaceutical active ingredients, such as drugs, nutrionals, cosmeceuticals and diagnostic agents.

55 Claims, 4 Drawing Sheets

US 6,569,463 B2

SOLID CARRIERS FOR IMPROVED DELIVERY OF HYDROPHOBIC ACTIVE INGREDIENTS IN PHARMACEUTICAL COMPOSITIONS

This application is a Divisional of Ser. No. 09/447,690 filed Nov. 23, 1999 now U.S. Pat. No. 6,248,363.

FIELD OF THE INVENTION

The present invention relates to pharmaceutical delivery systems for pharmaceutical active ingredients, such as drugs, nutritionals, cosmeceuticals, and diagnostic agents. In particular, the present invention provides compositions and dosage forms including solid carriers for improved delivery of pharmaceutical active ingredients.

BACKGROUND

Hydrophobic active ingredients, such as progesterone, cyclosporine, itraconazole and glyburide present delivery challenges due to their poor aqueous solubility and slow dissolution rate. Several conmmercial products of these hydrophobic drugs are available, the various products using different methods to try to enhance in vivo performance. One approach is size reduction by micronization, such as in Prometrium (micronized progesterone) and Micronase (micronized glyburide). Other approaches include size reduction in emulsion formulations, such as in Sandimmune (cyclosporine emulsion) and NeOral (cyclosporine microemulsion). These approaches suffer from several disadvantages. Micronization/nanonization presents processing and stability challenges, as well as dissolution limitations, since the micronized/nanosized drug still possesses a high degree of crystallinity. Liquid formulations present drug precipitation and packaging challenges, due to solvent evaporation. Moreover, non-solid formulations are more prone to chemical instability and capsule-shell incompatibility, leading to the possibility of leakage upon storage.

For hydrophilic active ingredients, the formulation challenges are different. Although these compounds are readily soluble in the aqueous gastrointestinal environment, they are poorly absorbed, due to poor membrane permeability and/or enzymatic degradation. Surfactants and lipophilic additives have been reported to improve membrane permeability; see, e.g., LeCluyse and Sutton, "In vitro models for selection of development candidates. Permeability studies to define mechanisms of absorption enhancement", *Advanced Drug Delivery Reviews*, 23, 163–183 (1997). However, these compositions fail to maintain effective levels and type of enhancers for bioacceptable absorption enhancement. Most solid dosage forms of hydrophilic active ingredients exhibit poor or no absorption of the active. Moreover, these non-solid formulations suffer from the disadvantages of chemical instability, leakage and capsule shell incompatibility as discussed above.

Solid carriers for pharmaceutical active ingredients offer potential advantages over micronized drugs, emulsions or solubilized formulations. Solid carriers, typically of size less than about 2 mm, can easily pass through the stomach, thus making the performance less prone to gastric emptying variability. Further, the problems of leakage and other disadvantages of liquid formulations are not present in solid carrier formulations. To date, however, such solid carrier formulations generally have been limited to a few specific drugs, due to difficulties in formulating appropriate drug/excipient compositions to effectively coat the active ingredient onto a carrier particle.

Conventional solid dosage forms of hydrophobic active ingredients, such as tablets, or multiparticulates in capsules, often exhibit slow and incomplete dissolution and subsequent absorption. These formulations often show a high propensity for biovariability and food interactions of the active ingredient, resulting in restrictive compliance/labeling requirements.

Due to the slow dissolution arid dependence on gastric emptying, solid dosage forms often delay the onset of some hydrophobic active ingredients.

Thus, there is a need for pharmaceutical compositions and dosage forms, and methods therefor, that do not suffer from the foregoing disadvantages.

SUMMARY OF THE INVENTION

It is an object of the invention to provide solid pharmaceutical compositions having active ingredients in a rapid dissolvable and more solubilized state herein.

It is another object of the invention to provide solid pharmaceutical compositions having more rapid dissolution upon administration to a patient.

It is another object of the invention to provide solid pharmaceutical compositions having more sustained and complete solubilization upon administration to a patient.

It is another object of the invention to provide solid pharmaceutical compositions capable of delivery a wide variety of pharmaceutical active ingredients.

It is another object of the invention to provide solid pharmaceutical compositions of coated substrate materials without the need for binders.

It is another object of the invention to provide solid pharmaceutical compositions having increased chemical stability of the active ingredient.

It is another object of the invention to provide solid pharmaceutical compositions capable of improving the absorption and/or bioavailability of a pharmaceutical active ingredient.

It is another object of the invention to provide solid pharmaceutical compositions having better protection of the upper gastrointestinal tract from untoward effects of the active ingredient.

It is another object of the present invention to provide solid pharmaceutical compositions capable of improving the palatability of or masking the taste of unpalatable pharmaceutical active ingredients.

In accordance with these and other objects, the present invention provides solid pharmaceutical compositions for improved delivery of a wide variety of pharmaceutical active ingredients contained therein or separately administered.

In one embodiment, the solid pharmaceutical composition includes a solid carrier, the solid carrier including a substrate and an encapsulation coat on the substrate. The encapsulation coat includes at least one ionic or non-ionic hydrophilic surfactant. Optionally, the encapsulation coat can include a pharmaceutical active ingredient, a lipophilic component such as a lipophilic surfactant or a triglyceride, or both a pharmaceutical active ingredient and a lipophilic component.

In another embodiment, the solid pharmaceutical composition includes a solid carrier, the solid carrier including a substrate and an encapsulation coat on the substrate. The encapsulation coat includes a lipophilic component, such as a lipophilic surfactant or a triglyceride. Optionally, the encapsulation coat can include a pharmaceutical active ingredient, an-ionic or non-ionic hydrophilic surfactant, or both a pharmaceutical active ingredient and a hydrophilic surfactant.

In another embodiment, the solid pharmaceutical composition includes a solid carrier, the solid carrier including a substrate and an encapsulation coat on the substrate. The encapsulation coat includes a pharmaceutical active ingredient and an ionic or non-ionic hydrophilic surfactant; a pharmaceutical active ingredient and a lipophilic component such as a lipophilic surfactant or a triglyceride; or a pharmaceutical active ingredient and both a hydrophilic surfactant and a lipophilic component.

In another embodiment, the solid pharmaceutical composition includes a solid carrier, wherein the solid carrier is formed of at least two components selected from the group consisting of pharmaceutical active ingredients; ionic or non-ionic hydrophilic surfactants; and lipophilic components such as lipophilic surfactants and triglycerides.

In other aspects, the present invention also provides dosage forms of any of the solid pharmaceutical compositions, and methods of using the solid pharmaceutical compositions.

These and other objects and features of the present invention will become more fully apparent from the following description and appended claims, or may be learned by the practice of the invention as set forth hereinafter.

BRIEF DESCRIPTION OF THE DRAWINGS

In order to illustrate the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
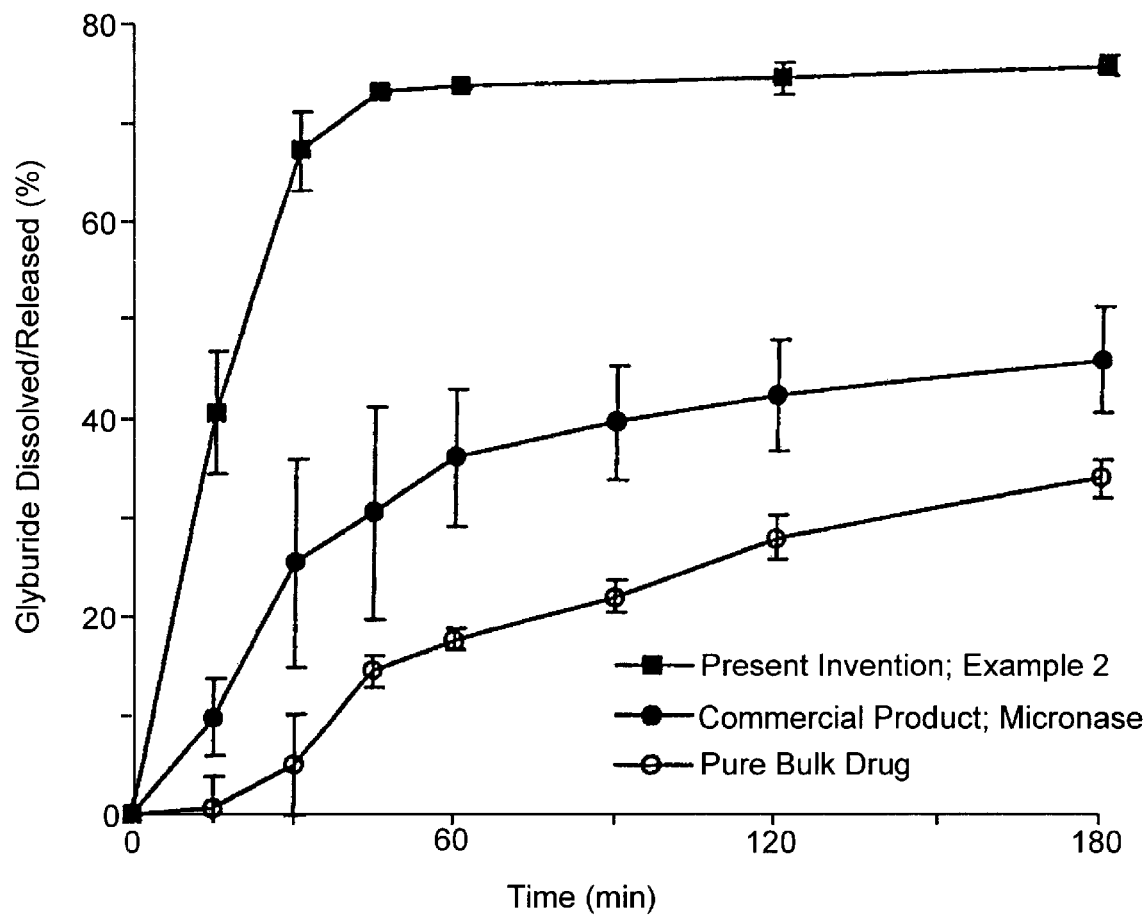
FIG. 1 is a graph showing the extent of dissolution/release of glyburide as a function of time for a composition according to the present invention and two prior art compositions.

The present invention provides solid pharmaceutical compositions for improved delivery of a wide variety of pharmaceutical active ingredients contained therein or separately administered. In one embodiment, the solid pharmaceutical composition includes a solid carrier, the solid carrier including a substrate and an encapsulation coat on the substrate. The encapsulation coat can include different combinations of pharmaceutical active ingredients, hydrophilic surfactant, lipophilic surfactants and triglycerides. In another embodiment, the solid pharmaceutical composition includes a solid carrier, the solid carrier being formed of different combinations of pharmaceutical active ingredients, hydrophilic surfactant, lipophilic surfactants and triglycerides. These and other embodiments, as well as preferred aspects thereof, are described in more detail below.

It should be appreciated that any of the components of the compositions of the present invention can be used as supplied commercially, or can be preprocessed by agglomeration, air suspension chilling, air suspension drying, balling, coacervation, comminution, compression, pelletization, cryopelletization, extrusion, granulation, homogenization, inclusion complexation, lyophilization, melting, mixing, molding, pan coating, solvent dehydration, sonication, spheronization, spray chilling, spray congealing, spray drying, or other processes known in the art. The various components can also be pre-coated or encapsulated. These various processes and coatings are described in more detail below.

1. Pharmaceutical Active Ingredients

In the embodiments of the present invention which include active ingredients, the active ingredients suitable for use in the pharmaceutical compositions and methods of the present invention are not particularly limited, as the compositions are surprisingly capable of effectively delivering a wide variety of active ingredients. The active ingredient can be hydrophilic, lipophilic, amphiphilic or hydrophobic, and can be solubilized, dispersed, or partially solubilized and dispersed, in the encapsulation coat. Alternatively, the active ingredient can be provided separately from the solid pharmaceutical composition, such as for co-administration. Such active ingredients can be any compound or mixture of compounds having therapeutic or other value when administered to an animal, particularly to a mammal, such as drugs, nutrients, cosmeceuticals, diagnostic agents, nutritional agents, and the like. It should be appreciated that the categorization of an active ingredient as hydrophilic or hydrophobic may change, depending upon the particular salts, isomers, analogs and derivatives used.

In one embodiment, the active ingredient agent is hydrophobic. Hydrophobic active ingredients are compounds with little or no water solubility. Intrinsic water solubilities (i.e., water solubility of the unionized form) for hydrophobic active ingredients are less than about 1% by weight, and typically less than about 0.1% or 0.01% by weight. In a particular aspect of this embodiment, the active ingredient is a hydrophobic drug. In other particular aspects, the active ingredient is a nutrient, a cosmeceutical, a diagnostic agent or a nutritional agent.

Suitable hydrophobic active ingredients are not limited by therapeutic category, and can be, for example, analgesics, anti-inflammatory agents, antihelmimthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malariale, anti-migrainc agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

Specific, non-limiting examples of suitable hydrophobic active ingredients are: acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, and zopiclone. Of course, salts, isomers and derivatives of the above-listed hydrophobic active ingredients may also be used, as well as mixtures.

Among the above-listed hydrophobic active ingredients, preferred active ingredients include: acetretin, albendazole, albuterol, aminoglutethimide, amiodarone, amlodipine, amphetamine, amphotericin B, atorvastatin, atovaquone, azithromycin, baclofen, benzonatate, bicalutanide, busulfan, butenafine, calcifediol, calcipotriene, calcitriol, camptothecin, capsaicin, carbamezepine, carotenes, celecoxib, cerivastatin, chlorpheniramine, cholecalciferol, cimetidine, cinnarizinc, ciprofloxacin, cisapride, citrizine, clarithromycin, clemastine, clomiphene, codeine, coenzyme Q10, cyclosporin, danazol, dantrolene, dexchlorpheniramine, diclofenac, digoxin, dehydroepiandrosterone, dihydroergotamine, dihydrotachysterol, dirithromycin, donepezil, efavirenz, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irinotecan, isotretinoin, itraconazole, ivermectin, ketoconazole, ketorolac, lamotriginc, lansoprazole, leflunomide, loperamnide, loratadine, lovastatin, L-thryroxine, lutein, lycopene, mifepristone, mefloquine, megestrol acetate, methdone, methoxsalen, metronidazole, miconazole, midazolam, miglitol, mitoxantrone, medroxyprogesterone, montelukast, nabumetone, nalbuphine, naratriptan, nelfinavir, nilutanide, nitrofurantoin, nizatidine, omeprazole, oestradiol, oxaprozin, paclitaxel, paracalcitol, pentazocine, pioglitazone, pizofetin, pravastatin, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sibutramine, sildenafil citrate, simvastatin, sirolimus, spironolactone, sumatriptan, tacrine, tacrolimus, tamoxifen, tamsulosin, targretin, tazarotene, teniposide, terbinafine, tetrahydrocannabinol, tiagabine, tizanidine, topiramate, topotecan, toremifene, tramadol, tretinoin, troglitazone, trovafloxacin, verteporfin, vigabatrin, vitamin A, vitamin D, vitamin E, vitamin K, zafirlukast, zilcuton, zolmitriptan, zolpidem, zopiclone, pharmaceutically acceptable salts, isomers and derivatives thereof, and mixtures thereof.

Particularly preferred hydrophobic active ingredients include: acetretin, albuterol, aminoglutethimide, amiodarone, amlodipine, amprenavir, atorvastatin, atovaquone, baclofen, benzonatate, bicalutanide, busulfan, calcifediol, calcipotriene, calcitriol, camptothecin, capsaicin, carbamezepine, carotenes, celecoxib, chlorpheniramine, cholecaliferol, cimetidine, cinnarizine, cisapride, cetirizine, clemastine, coenzyme Q10, cyclosporin, danazol, dantrolene, dexchlorpheniramine, diclofenac, dehydroepiandrosterone, dihydroergotamine, dihydrotachysterol, efavirenz, ergocalciferol, ergotamine, essential fatty acid sources, etodolac, etoposide, famotidine, fenofibrate, fexofenadine, finasteride, fluconazole, flurbiprofen, fosphenytoin, frovatriptan, furazolidone, glibenclamide, glipizide, glyburide, glimepiride, ibuprofen, irinotecan, isotretinoin, itraconazole, ivermectin, ketoconazole, ketorolac, lamotrigine, lansoprazole, leflunomide, loperamide, loratadine, lovastatin, L-thryroxine, lutein, lycopene, medroxyprogesterone, mifepristone, megestrol acetate, methoxsalen, metronidazole, miconazole, miglitol, mitoxantrone, montelukast, nabumetone, naratriptan, nelfinavir, nilutanide, nitrofurantoin, nizatidine, omeprazole, oestradiol, oxaprozin, paclitaxel, paracalcitol, pioglitazone, pizofetin, pranlukast, probucol, progesterone, pseudoephedrine, rabeprazole, raloxifene, rofecoxib, repaglinide, rifabutine, rifapentine, rimexolone, ritanovir, rizatriptan, rosiglitazone, saquinavir, sildenafil citrate, simvastatin, sirolimus, tacrolimus, tamoxifen, tamsulosin, targretin, tazarotene, teniposide, terbenafine, tetrahydrocannabinol, tiagabine, tizanidine, topiramate, topotecan, toremifene, tramadol, tretinoin, troglitazone, trovafloxacin, ubidecarenone, vigabatrin, vitamin A, vitamin D, vitamin E, vitamin K, zafirlukast, zileuton, zolmitriptan, pharmaceutically acceptable salts, isomers and derivative thereof, and mixtures thereof.

Most preferred hydrophobic active ingredients include: amlodipine, amprenavir, atorvastatin, atovaquone, celecoxib, cisapride, coenzyme Q10, cyclosporin, famotidine, fenofibrate, fexofenadine, finasteride, ibuprofen, itraconazole, lansoprazole, loratadine, lovastatin, megestrol acetate, montelukast, nabumetone, nizatidine, omeprazole, oxaprozin, paclitaxel, paracalcitol, pioglitazone, pranlukast, progesterone, pseudoephedrine, rabeprazole, rapamycin, rofecoxib, repaglinide, rimexolone, ritanovir, rosiglitazone, saquinavir, sildenafil citrate, simvastatin, sirolimus, tacrolimus, tamsulosin, teniposide, terbenafine, tetrahydrocannabinol, tiagabine, tizanidine, tramadol, troglitazone, vitamin A, vitamin D, vitamin E, zafirlukast, zileuton, pharmaceutically acceptable salts, isomers and derivatives thereof, and mixtures thereof.

In another embodiment, the active ingredient is hydrophilic. Amphiphilic compounds are also included within the class of hydrophilic active ingredients. Apparent water solubilities for hydrophilic active ingredients are greater than about 0.1% by weight, and typically greater than about 1% by weight. In a particular aspect of this embodiment, the hydrophilic active ingredient is a hydrophilic drug. In other particular aspects, the hydrophilic active ingredient is a cosmeceutical, a diagnostic agent, or a nutritional agent.

Suitable hydrophilic active ingredients are not limited by therapeutic category, and can be, for example, analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastrointestinal agents, histamine receptor antagonists, keratolytics, lipid regulating agents, anti-anginal agents, cox-2 inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof Likewise, the hydrophilic active ingredient can be a cytokine, a peptidomimetic, a peptide, a protein, a toxoid, a serum, an antibody, a vaccine, a nucleoside, a nucleotide, a portion of genetic material, a nucleic acid, or a mixture thereof.

Specific, non-limiting examples of suitable hydrophilic active ingredients include: acarbose; acyclovir; acetyl cysteine; acetylcholine chloride; alatrofloxacin; alendronate; aglucerase; amantadine hydrochloride; ambenomium; amifostine; amiloride hydrochloride; aminocaproic acid; amphotericin B; antihemophilic factor (human), antihemophilic factor (porcine); antihemophilic factor (recombinant), aprotinin; asparaginase; atenolol; atracurium besylate; atropine; azithromycin; aztreonam; BCG vaccine; bacitracin; becalermin; belladona; bepridil hydrochloride; bleomnycin sulfate; calcitonin human; calcitonin salmon; carboplatin; capecitabine; capreomycin sulfate; cefamandole nafate; cefazolin sodium; cefepime hydrochloride; cefixime; cefonicid sodium; cefoperazone; cefotetan disodium; cefotaxime; cefoxitin sodium; ceftizoxime; ceftriaxone; cefuroxime axetil; cephalexin; cephapirin sodium; cholera vaccine; chorionic gonadotropin; cidofovir; cisplatin; cladribine; clidinium bromide; clindamycin and clindamycin derivatives; ciprofloxacin; clodronate; colistimethate sodium; colistin sulfate; corticotropin; cosyntropin; cromolyn sodium; cytarabine; dalteparin sodium; danaparoid; desferrioxamine; denileukin diflitox; desmopressin; diatrizoate meglumine and diatrizoate sodium; dicyclomine; didanosine; dirithromycin; dopamine hydrochloride; dornase alpha; doxacurium chloride; doxorubicin; etidronate disodium; enalaprilat; enkephalin; enoxaparin; enoxaprin sodium; ephedrine; epinephrine; epoetin alpha; erythromycin; esmolol hydrochloride; factor IX; famciclovir; fludarabine; fluoxetine; foscarnet sodium; ganciclovir; granulocyte colony stimulating factor, granulocyte-macrophage stimulating factor; growth hormones—recombinant human; growth hormone—bovine; gentamycin; glucagon; glycopyrolate; gonadotropin releasing hormone and synthetic analogs thereof; GnRH; gonadorelin; grepafloxacin; haemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human, insulin lispro; insulin procine; insulin NPH; insulin aspart; insulin glargine; insulin detemir; interferon alpha; interferon beta; ipratropium bromide; ifosfamide; Japanese encephalitis virus vaccine; lamivudine; leucovorin calcium; leuprolide acetate, levofloxacin; lincomycin and lincomycin derivatives; lobucavir; lomefloxacin; loracarbef; mannitol; is measles virus vaccine; meningococcal vaccine; menotropins; mepenzolate bromide; mesalamine; methenamine; methotrexate; methscopolamine; metformin hydrochloride; metoprolol; mezocillin sodium; mivacurium chloride; mumps viral vaccine; nedocromil sodium; neostigmine bromide; neostigmine methyl sulfate; neurontin; norfloxacin; octreotide acetate; ofloxacin; olpadronate; oxytocin; pamidronate disodium; pancuronium bromide; paroxetine; perfloxacin; pentamidine isethionate; pentostatin; pentoxifylline; periciclovir; pentagastrin; pentholamine mesylate; phenylalanine; physostigmine salicylate; plague vaccine; piperacillin sodium; platelet derived growth factor-human; pneumococcal vaccine polyvalent; poliovirus vaccine inactivated; poliovirus vaccine live (OPV); polymyxin B sulfate; pralidoxime chloride; pramlintide, pregabalin; propafenone; propenthaline bromide; pyridostigmine bromide; rabies vaccine; residronate; ribavarin; rimantadine hydrochloride; rotavirus vaccine; salmeterol xinafoate; sinealide; small pox vaccine; solatol; somatostatin; sparfloxacin; spectinomycin; stavudine; streptokinase; streptozocin; suxamethonium chloride; tacrine hydrochloride; terbutaline sulfate; thiopeta; ticarcillin; tiludronate; timolol; tissue type plasminogen activator; TNFR:Fc; TNK-tPA; trandolapril; trimetrexate gluconate; trospectinomycin; trovafloxacin; tubocurarine chloride; tumor necrosis factor; typhoid vaccine live; urea; urokinase; vancomycin; valacyclovir; valsartan; varicella virus vaccine live; vasopressin and vasopressin derivatives; vecuronium bromide; vinblastine; vincristine; vinorelbine; vitamin B12; warfarin sodium; yellow fever vaccine; zalcitabine; zanamivir; zolendronate; zidovudine; pharmaceutically acceptable salts, isomers and derivatives thereof; and mixtures thereof.

Among the above-listed hydrophilic active ingredients, preferred active ingredients include acarbose; acyclovir; atracurium besylate; alendronate; aglucerase; amantadine hydrochloride: amphotericin B; antihemophilic factor (human); antihemophilic factor (porcine); antihemophilic factor (recombinant; azithromycin; calcitonin human; calcitonin salmon; capecitabine; cefazolin sodium; cefonicid sodium, cefoperazone; cefoxitin sodium; ceftizoxime;

ceftriaxone; ceftizoxime axetil; cephalexin; chorionic gonadotropin; cidofovir; cladribine; clindamycin and clindamycin derivatives; corticotropin; cosyntropin; cromolyn sodium; cytarabine; dalteparin sodium; danaparoid; desmopressin; didanosine; dirithromycin; etidronate disodium; enoxaprin sodium; epoetin alpha; factor IX; famciclovir; fludarabine; foscarnet sodium; ganciclovir; granulocyte colony stimulating factor; granulocyte-macrophage stimulating factor; growth hormones—recombinant human; growth hormone—Bovine; gentamycin; glucagon; gonadotropin releasing hormone and synthetic analogs thereof; GnRH; gonadorelin; haemophilus B conjugate vaccine; Hepatitis A virus vaccine inactivated; Hepatitis B virus vaccine inactivated; heparin sodium; indinavir sulfate; influenza virus vaccine; interleukin-2; interleukin-3; insulin-human; insulin lispro; insulin procine; insulin NPH; insulin aspart; insulin glargine; insulin detemir; interferon alpha; interferon beta; ipratropium bromide; ifosfamide; lamivudine; leucovorin calcium; leuprolide acetate; lincomycin and lincomycin derivatives; metformin hydrochloride; nedocromil sodium; neostigmine bromide; neostigmine methyl sulfate; neurontin; octreotide acetate; olpadronate; pamidronate disodium; pancuronium bromide; pentamidine isethionate; pentagastrin; physostigmine salicylate; poliovirus vaccine live (OPV); pyridostigmine bromide; residronate; ribavarin; rimantadine hydrochloride; rotavirus vaccine; salmeterol xinafoate; somatostatin; spectinomycin; stavudine; streptokinase; ticarcillin; tiludronate; tissue type plasminogen activator; TNFR:Fc; TNK-tPA; trimetrexate gluconate; trospectinomycin; tumor necrosis factor; typhoid vaccine live; urokinase; vancomycin; valacyclovir; vasopressin and vasopressin derivatives; vinblastin; vincristine; vinorelbine; warfarin sodium; zalcitabine; zanamivir, zidovudine; pharmaceutically acceptable salts, isomers and derivatives thereof; and mixtures thereof.

Most preferred hydrophilic active ingredients include acarbose; alendronate; amantadine hydrochloride, azithromycin; calcitonin human; calcitonin salmon; ceftriaxone; cefuroxime axetil; chorionic gonadotropin; cromolyn sodium; daltaperin sodium; danaproid; desmopressin; didanosine; etidronate disodium; enoxaprin sodium; epoetin alpha; factor IX; famiciclovir; foscarnet sodium; ganciclovir; granulocyte colony stimulating factor; granulocyte-macrophage stimulating factor; growth hormones—recombinant human; growth hormone—Bovine; glucagon; gonadotropin releasing hormone and synthetic analogs thereof; GnRH; gonadorelin; heparin sodium; indinavir sulfate; influenza virus vaccine; interleukin-2; interleukin-3; insulin-human; insulin lispro; insulin procine interferon alpha; interferon beta; leuprolide acetate; metformin hydrochloride; nedocromil sodium; neostigmine bromide; neostigmine methyl sulfate; neutontin; octreotide acetate; olpadronate; pamidronate disodium; residronate; rimantadine hydrochloride; salmetrol xinafoate; somatostatin; stavudine; ticarcillin; tiludronate; tissue type plasminogen activator; TNFR:Fc; TNK-tPA; tumor necrosis factor; typhoid vaccine live; vancomycin; valacyclovir; vasopressin and vasopressin derivatives; zalcitabine; zanamivir; zidovudine; pharmaceutically acceptable salts, isomers and derivatives thereof; and mixtures thereof.

2. Surfactants

Various embodiments of the invention, as described in more detail below, include a hydrophilic surfactant. Hydrophilic surfactants can be used to provide any of several advantageous characteristics to the compositions, including: increased solubility of the active ingredient in the solid carrier; improved dissolution of the active ingredient; improved solubilization of the active ingredient upon dissolution; enhanced absorption and/or bioavailability of the active ingredient, particularly a hydrophilic active ingredient; and improved stability, both physical and chemical, of the active ingredient. The hydrophilic surfactant can be a single hydrophilic surfactant or a mixture of hydrophilic surfactants, and can be ionic or non-ionic.

Likewise, various embodiments of the invention include a lipophilic component, which can be a lipophilic surfactant, including a mixture of lipophilic surfactants, a triglyceride, or a mixture thereof. The lipophilic surfactant can provide any of the advantageous characteristics listed above for hydrophilic surfactants, as well as further enhancing the function of the surfactants. These various embodiments are described in more detail below. For convenience, the surfactants are described in this section, and the triglycerides in the section that follows.

As is well known in the art, the terms "hydrophilic" and "lipophilic" are relative terms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and lipophilicity of non-ionic amphiphilic compounds is the hydrophilic-lipophilic balance (the "HLB" value). Surfactants with lower HLB values are more lipophilic, and have greater solubility in oils, whereas surfactants with higher HLB values are more hydrophilic, and have greater solubility in aqueous solutions.

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, lipophilic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, *J. Pharm. Sciences,* 79(1), 87–88 (1990)). Likewise, for certain polypropylene oxide containing block copolymers (poloxamers, available commercially as PLURONIC® surfactants, BASF Corp.), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or lipophilicity for use in the present invention, as described herein.

Surfactants can be any surfactant suitable for use in pharmaceutical compositions. Suitable surfactants can be anionic, cationic, zwitterionic or non-ionic. Such surfactants can be grouped into the following general chemical classes detailed in the Tables herein. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

It should be emphasized that the invention is not limited to the surfactants in the Tables, which show representative, but not exclusive, lists of available surfactants. In addition, refined, distilled or fractionated surfactants, purified fractions thereof, or re-esterified fractions, are also within the scope of the invention, although not specifically listed in the Tables.

2.1. Polyethoxylated Fatty Acids

Although polyethylene glycol (PEG) itself does not function as a surfactant, a variety of PEG-fatty acid esters have useful surfactant properties. Examples of polyethoxylated fatty acid monoester surfactants commercially available are shown in Table 1.

TABLE 1

PEG-Fatty Acid Monoester Surfactants

| COMPOUND | COMMERCIAL PRODUCT (Supplier) | HLB |
|---|---|---|
| PEG 4–100 monolaurate | Crodet L series (Croda) | >9 |
| PEG 4–100 monooleate | Crodet O series (Croda) | >8 |
| PEG 4–100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400–1000 monostearate | Cithrol MS series (Croda) | >10 |
| PEG-1 stearate | Nikkol MYS-IEX (Nikko), Coster KI (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200ML (Stepan), LIPOPEG 2L (LIPO Chem.) | 9.3 |
| PEG-4 oleate | Mapeg ® 200 MO (PPG), Kessco ® PEG200 MO (Stepan), | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stepan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco ® PEG300 ML (Stepan) | 11.4 |
| PEG-7 laurate | Lauridac 7 (Condea) | 13 |
| PEG-6 stearate | Kessco ® PEG300 MS (Stepan) | 9.7 |
| PEG-8 laurate | Mapeg ® 400 ML (PPG), LIPOPEG 4DL(Lipo Chem.) | 13 |
| PEG-8 oleate | Mapeg ® 400 MO (PPG), Emulgante A8 (Condea); Kessco PEG 400 MO (Stepan) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor 59 (BASF) | >10 |
| PEG-10 laurate | Nikkol MYL-10 (Nikko), Lauridac 10 (Croda) | 13 |

TABLE 1-continued

PEG-Fatty Acid Monoester Surfactants

| COMPOUND | COMMERCIAL PRODUCT (Supplier) | HLB |
|---|---|---|
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600ML (Stepan) | 15 |
| PEG-12 oleate | Kessco ® PEG 600MO (Stepan) | 14 |
| PEG-12 ricinoleate | (CAS #9004-97-1) | >10 |
| PEG-12 stearate | Mapeg ® 600 MS (PPG), Kessco ® PEG 600MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet 0–100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf) | >10 |

2.2 PEG-Fatty Acid Diesters

Polyethylene glycol (PEG) fatty acid diesters are also suitable for use as surfactants in the compositions of the present invention. Representative PEG-fatty acid diesters are shown in Table 2.

TABLE 2

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 / 6 |
| PEG-4 dioleate | Mapeg ® 200 DO (PPG), | 6 |
| PEG-4 distearate | Kessco ® 200 DS (Stepan) | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO(Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO(Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |

TABLE 2-continued

PEG-Fatty Acid Diester Surfactants

| COMPOUND | COMMERCIAL PRODUCT (Supplier) | HLB |
|---|---|---|
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

2.3 PEG-Fatty Acid Mono- and Di-ester Mixtures

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 3.

TABLE 3

PEG-Fatty Acid Mono-and Diester Mixtures

| COMPOUND | COMMERCIAL PRODUCT (Supplier) | HLB |
|---|---|---|
| PEG 4–150 mono, dilaurate | Kessco ® PEG 200–6000 mono, dilaurate (Stepan) | |
| PEG 4–150 mono, dioleate | Kessco ® PEG 200–6000 mono, dioteate (Stepan) | |
| PEG 4–150 mono, distearate | Kessco ® 200–6000 mono, distearate (Stepan) | |

2.4 Polyethylene Glycol Glycerol Fatty Acid Esters

Suitable PEG glycerol fatty acid esters are shown in Table 4.

TABLE 4

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

2.5. Alcohol—Oil Transesterification Products

A large number of surfactants of different degrees of lipophilicity or hydrophilicity can be prepared by reaction of alcohols or polyalcohols with a variety of natural and/or hydrogenated oils. Most commonly, the oils used are castor oil or hydrogenated castor oil or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Representative surfactants of this class suitable for use in the present invention are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6–7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6–7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70(Croda) | 15 |
| PEG-60 almond glycerides | Crovol A70 (Croda) | 15 |
| PEG-4 caprylic/capric triglyceride | Labrafac ® Hydro (Gattefosse), | 4–5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Huls), Glycerox 767 (Croda) | 19 |

TABLE 5-continued

Transesterification Products of Oils and Alcohols

| COMPOUND | COMMERCIAL PRODUCT (Supplier) | HLB |
|---|---|---|
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/ tetracaprate | Liponate PE-810 (Lipo Chem.), Crodamol PTC (Croda) | <10 |
| Pentaerythrityl tetraoctanoate | Nikkol Pentarate 408 (Nikko) | |

2.6. Polyglycerized Fatty Acids

Polyglycerol esters of fatty acids are also suitable surfactants for the present invention. Examples of suitable polyglyceryl esters are shown in Table 6.

TABLE 6

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5–7 |
| Polyglyceryl-2 oleate | Nikkol DGMO (Nikko) | 5–7 |
| Polyglyceryl-2 isostearate | Nikkol DGMIS (Nikko) | 5–7 |
| Polyglyceryl-3 oleate | Caprol ® 3G0 (ABITEC), Drewpol 3-1-O (Stepan) | 6.5 |
| Polyglyceryl-4 oleate | Nikkol Tetraglyn 1-O (Nikko) | 5–7 |
| Polyglyceryl-4 stearate | Nikkol Tetraglyn 1-S (Nikko) | 5–6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | |
| Polyglyceryl-10 linoleate | Nikkol Decaglyn I-LN (Nikko) | 12 |
| Polyglyceryl-6 pentaoleate | Nikkol Hexaglyn 5-O (Nikko) | <10 |
| Polyglyceryl-3 dioleate | Cremophor G032 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decagtyn 7-O (Nikko) | 3 |
| Polyglyceryl-10 tetraoleate | Caprol ® 10G40 (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-10 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3–20 |

2.7. Propylene Glycol Fatty Acid Esters

Esters of propylene glycol and fatty acids are suitable surfactants for use in the present invention. Examples of surfactants of this class are given in Table 7.

TABLE 7

Propylene Glycol Fatty Acid Esters

| COMPOUND | COMMERCIAL PRODUCT (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3–4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-06 (Eastman) | <10 |
| Propylene dicaprylate/dicaprate | glycol Captex ® 200 (ABITEC), Miglyol ® 840 (Huls), Neobee ® M-20 (Stepan) | >6 |
| Propylene glycol dioctanoate | Captex ® 800 (ABITEC) | |
| Propylene caprylate/caprate | glycol LABRAFAC PG (Gattefosse) | >6 |
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

2.8. Mixtures of Propylene Glycol Esters—Glycerol Esters

In general, mixtures of surfactants are also suitable for use in the present invention. In particular, mixtures of propylene glycol fatty acid esters and glycerol fatty acid esters are suitable and are commercially available. Examples of these surfactants are shown in Table 8.

TABLE 8

Glycerol/Propylene Glycol Fatty Acid Esters

| COMPOUND | COMMERCIAL PRODUCT (Supplier) | HLB |
|---|---|---|
| Oleic | ATMOS 300, ARLACEL 186 (ICI) | 3–4 |
| Stearic | ATMOS 150 | 3–4 |

2.9. Mono- and Diglycerides

A particularly important class of surfactants is the class of mono- and diglycerides. These surfactants are generally lipophilic. Examples of these surfactants are given in Table 9.

TABLE 9

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |

TABLE 9-continued

Mono- and Diglyceride Surfactants

| COMPOUND | COMMERCIAL PRODUCT (Supplier) | HLB |
|---|---|---|
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3–4 |
| Glyceryl monooleate (C18:1) | PECEOL (Gattefosse), Hodag GMO-D, Nikkol MGO (Nikko) | 3–4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3–4 |
| Glycerol monooleate/linoleate | OLICINE (Gattefosse) | 3–4 |
| Glycerol monolinoleate | Maisine (Gattefosse), MYVEROL 18–92, Myverol 18-06 (Eastman) | 3–4 |
| Glyceryl ricinoleate | Softigen ® 701 (Huls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS. (ABITEC), Myvaplex (Eastman), IMWITOR ® 191 (Huls), CUTINA GMS, Aldo ® MS (Lonza), Nikkol MGS series (Nikko) | 5–9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grünau GmbH) | <10 |
| Glyceryl laurate | Inwitor ® 312 (Huls), Monomuls ® 90-45 (Grünau GmbH), Aldo ® MLD (Lonza) | 4 |
| Glyceryl citrate/lactate/oleate/linoieate | Imwitor ® 375 (Huls) | <10 |
| Glyceryl caprylate | Imwitor ® 308 (Huls), Capmul ® MCM8 (ABITEC) | 5–6 |
| Glyceryl caprylate/caprate | Capmul ® MCM (ABITEC) | 5–6 |
| Caprylic acid mono, diglycerides | Imwitor ® 988 (Huls) | 5–6 |
| Caprylic/capric glycerides | Imwitor ® 742 (Huls) | <10 |
| Mono-and diacetylated monoglycerides | Myvacet ® 9–45, Myvacet ® 9–40, Myvacet ® 9-08 (Eastman), Lamegin ® (Grünau) | 3.8–4 |
| Glyceryl monostearate | Aldo ® MS, Arlacel 129 (ICI), LIPO GMS (Lipo Chem.), Imwitor ® 191 (Huls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3–4 |
| Glyceryl dioleate | Capmul ® GDO (ABITEC) | 3–4 |
| Glycerol esters of fatty acids | GELUCIRE 39/01 (Gattefosse), GELUCIRE 43/01 (Gattefosse), GELUCIRE 37/06 (Gattefosse) | 1, 6 |
| Dipalmitolein (C16:1) | (Larodan) | |
| 1, 2 and 1,3-diolein (C18:1) | (Larodan) | <10 |
| Dielaidin (C18:1) | (Larodan) | <10 |
| Dilinolein (C18:2) | (Larodan) | <10 |

2.10. Sterol and Sterol Derivatives

Sterols and derivatives of sterols are suitable surfactants for use in the present invention. These surfactants can be hydrophilic or lipophilic. Examples of surfactants of this class are shown in Table 10.

TABLE 10

Sterol and Sterol Derivative Surfactants

| COMPOUND | COMMERCIAL PRODUCT (Supplier) | HLB |
|---|---|---|
| Cholesterol, sitosterol, lanosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

2.11. Polyethylene Glycol Sorbitan Fatty Acid Esters

A variety of PEG-sorbitan fatty acid esters are available and are suitable for use as surfactants in the present invention. In general, these surfactants are hydrophilic, although several lipophilic surfactants of this class can be used. Examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PBG-6 sorbitan monostearate | Nikkol TS106 (Nikko) | 11 |
| PEG-20 sorbitan tristearate | Tween-65 (Atlas/ICI), Crillet 35 (Croda) | 11 |

TABLE 11-continued

PEG-Sorbitan Fatty Acid Esters

| COMPOUND | COMMERCIAL PRODUCT (Supplier) | HLB |
| --- | --- | --- |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

2.12. Polyethylene Glycol Alkyl Ethers

Ethers of polyethylene glycol and alkyl alcohols are suitable surfactants for use in the present invention. Examples of these surfactants are shown in Table 12.

TABLE 12

Polyethylene Glycol Alkyl Ethers

| COMPOUND | COMMERCIAL PRODUCT (Supplier) | HLB |
| --- | --- | --- |
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

2.13. Sugar Esters

Esters of sugars are suitable surfactants for use in the present invention. Examples of such surfactants are shown in Table 13.

TABLE 13

Sugar Ester Surfactants

| COMPOUND | COMMERCIAL PRODUCT (Supplier) | HLB |
| --- | --- | --- |
| Sucrose distearate | SUCRO ESTER 7 (Gattefosse), Crodesta F-10 (Croda) | 3 |
| Sucrose distearate/ monostearate | SUCRO ESTER 11 (Gattefosse), Crodesta F-110 (Croda) | 12 |
| Sucrose dipalmitate | | 7.4 |

TABLE 13-continued

Sugar Ester Surfactants

| COMPOUND | COMMERCIAL PRODUCT (Supplier) | HLB |
| --- | --- | --- |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

2.14. Polyethylene Glycol Alkyl Phenols

Several hydrophilic PEG-alkyl phenol surfactants are available, and are suitable for use in the present invention. Examples of these surfactants are shoe n in Table 14.

TABLE 14

Polyethylene Glycol Alkyl Phenol Surfactants

| COMPOUND | COMMERCIAL PRODUCT (Supplier) | HLB |
| --- | --- | --- |
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

2.15. Polyoxyethylene-Polyoxypropylene Block Copolymers

The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including Synperonic PE series (ICI); Pluronic® series (BASF), Emkalyx, Lutrol (BASF), Supronic, Monolan, Pluracare, and Plurodac. The generic term for these polymers is "poloxamer" (CAS 9003-11-6). These polymers have the formula:

$$HO(C_2H_4O)_a(C_3H_6O)_b(C_2H_4O)_aH$$

where "a" and "b" denote the number of polyoxyethylene and polyoxypropylene units, respectively.

Examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in $HO(C_2H_4O)_a(C_3H_6O)_b(C_2H_4O)_aH$ | | HLB |
| --- | --- | --- | --- |
| Poloxamer 105 | a = 11 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |

TABLE 15-continued

POE-POP Block Copolymers

| COMPOUND | a, b values in HO(C$_2$H$_4$O)$_a$(C$_3$H$_6$O)$_b$(C$_2$H$_4$O)$_a$H | | HLB |
|---|---|---|---|
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

2.16. Sorbitan Fatty Acid Esters

Sorbitan esters of fatty acids are suitable surfactants for use in the present invention. Examples of these surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

2.17. Lower Alcohol Fatty Acid Esters

Esters of lower alcohols (C$_2$ to C$_4$) and fatty acids (C$_8$ to C$_{18}$) are suitable surfactants for use in the present invention. Examples of these surfactants are shown in Table 17.

TABLE 17

Lower Alcohol Fatty Acid Ester Surfactants

| COMPOUND | COMMERCIAL PRODUCT (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

2.18. Ionic Surfactants

Ionic surfactants, including cationic, anionic and zwitterionic surfactants, are suitable hydrophilic surfactants for use in the present invention. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown in Table 18. For simplicity, typical counterions are shown in the entries in the Table. It will be appreciated by one skilled in the art, however, that any bioacceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |
| Sodium N-methyl taurocholate | |
| Sodium lithocholate | |
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |

TABLE 18-continued

Ionic Surfactants

| COMPOUND | HLB |
|---|---|
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

2.19 Unionized Ionizable Surfactants

Ionizable surfactants, when present in their unionized (neutral, non-salt) form, are lipophilic surfactants suitable for use in the compositions of the present invention. Particular examples of such surfactants include free fatty acids, particularly $C_6$–$C_{22}$ fatty acids, and bile acids. More specifically, suitable unionized ionizable surfactants include the free fatty acid and bile acid forms of any of the fatty acid salts and bile salts shown in Table 18.

2.20 Derivatives of Fat-Soluble Vitamins

Derivatives of oil-soluble vitamins, such as vitamins A, D, E, K, etc., are also useful surfactants for the compositions of the present invention. An example of such a derivative is tocopheryl PEG-1000 succinate (TPGS, available from Eastman).

2.21 Preferred Surfactants

Among the above-listed surfactants, several surfactants are preferred. In general, surfactants or mixtures of surfactants that solidify at ambient room temperature are most preferred. Also preferred are surfactants or mixtures of surfactants that solidify at ambient room temperature in combination with particular lipophilic components, such as triglycerides, or with addition of appropriate additives, such as viscosity modifiers, binders, thickeners, and the like.

Preferred non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; polyethoxylated fat-soluble vitamins or derivatives; and mixtures thereof.

More preferably, the non-ionic hydrophilic surfactant is selected from the group consisting of polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. The glyceride can be a monoglyceride, diglyceride, triglyceride, or a mixture.

Also preferred are non-ionic hydrophilic surfactants that are reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol is preferably glycerol, ethylene glycol, polyethylene glycol, sorbitol, propylene glycol, pentaerythritol, or a saccharide.

The hydrophilic surfactant can also be, or include as a component, an ionic surfactant. Preferred ionic surfactants include alkyl ammonium salts; bile acids and salts, analogues, and derivatives thereof; fusidic acid and derivatives thereof; fatty acid derivatives of amino acids, oligopeptides, and polypeptides; glyceride derivatives of amino acids, oligopeptides, and polypeptides; acyl lactylates; mono-,diacetylated tartaric acid esters of mono-, diglycerides; succinylated monoglycerides; citric acid esters of mono-,diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

More preferable ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono-,diacetylated tartaric acid esters of mono-,diglycerides; succinylated monoglycerides; citric acid esters of mono-diglycerides; carnitines; and mixtures thereof.

More specifically, preferred ionic surfactants arc lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Particularly preferred ionic surfactants are lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof, with the most preferred ionic surfactants being lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

Preferred lipophilic surfactants are alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; and polyoxyethylene hydrogenated vegetable oils.

As with the hydrophilic surfactants, lipophilic surfactants can be reaction mixtures of polyols and fatty acids, glycerides, vegetable oils, hydrogenated vegetable oils, and sterols.

Preferably, the lipophilic surfactant is selected from the group consisting of fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols.

More preferred are lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof, with glycerol fatty acid esters and acetylated glycerol fatty acid esters being most preferred. Among the glycerol fatty acid esters, the esters are preferably mono- or diglycerides, or mixtures of mono- and diglycerides, where the fatty acid moiety is a $C_6$ to $C_{22}$ fatty acid.

Also preferred are lipophilic surfactants which are the reaction mixture of polyols and fatty acids, glycerides, vegetable oils, hydrogenated vegetable oils, and sterols. Preferred polyols are polyethylene glycol, sorbitol, propylene glycol, and pentaerythritol.

3. Triglycerides

For compositions of the present invention that include a lipophilic component, the lipophilic component can be a lipophilic surfactant or a triglyceride. Preferred triglycerides are those which solidify at ambient room temperature, with or without addition of appropriate additives, or those which in combination with particular surfactants and/or active ingredients solidify at room temperature. Examples of triglycerides suitable for use in the present invention are shown in Table 19. In general, these triglycerides are readily available from commercial sources. For several triglycerides, representative commercial products and/or commercial suppliers are listed.

TABLE 19

Triglycerides

| Triglyceride | Commercial Source |
|---|---|
| Aceituno oil | |
| Almond oil | Super Refined Almond Oil (Croda) |
| Arachis oil | |
| Babassu oil | |
| Beeswax | |
| Blackcurrant seed oil | |
| Borage oil | |
| Buffalo ground oil | |
| Candlenut oil | |
| Canola oil | Lipex 108 (Abitec) |
| Castor oil | |
| Chinese vegetable tallow oil | |
| Cocoa butter | |
| Coconut oil | Pureco 76 (Abitec) |
| Coffee seed oil | |
| Corn oil | Super Refined Corn Oil (Croda) |
| Cottonseed oil | Super Refined Cottonseed Oil (Croda) |
| Crambe oil | |
| Cuphea species oil | |
| Evening primrose oil | |
| Grapeseed oil | |
| Groundnut oil | |
| Hemp seed oil | |
| Illipe butter | |
| Kapok seed oil | |
| Linseed oil | |
| Menhaden oil | Super Refined Menhaden Oil (Croda) |
| Mowrah butter | |
| Mustard seed oil | |
| Oiticica oil | |
| Olive oil | Super Refined Olive Oil (Croda) |
| Palm oil | |
| Palm kernel oil | |
| Peanut oil | Super Refined Peanut Oil (Croda) |
| Poppy seed oil | |
| Rapeseed oil | |
| Rice bran oil | |
| Safflower oil | Super Refined Safflower Oil (Croda) |
| Sal fat | |
| Sesame oil | Super Refined Sesame Oil (Croda) |
| Shark liver oil | Super Refined Shark Liver Oil (Croda) |
| Shea nut oil | |
| Soybean oil | Super Refined Soybean Oil (Croda) |
| Stillingia oil | |
| Sunflower oil | |
| Tall oil | |
| Tea seed oil | |
| Tobacco seed oil | |

TABLE 19-continued

Triglycerides

| Triglyceride | Commercial Source |
| --- | --- |
| Tung oil (China wood oil) | |
| Ucuhuba | |
| Vernonia oil | |
| Wheat germ oil | Super Refined Wheat Germ Oil (Croda) |
| Hydrogenated castor oil | Castorwax |
| Hydrogenated coconut oil | Pureco 100 (Abitec) |
| Hydrogenated cottonseed oil | Dritex C (Abitec) |
| Hydrogenated palm oil | Dritex PST (Abitec); Softisan 154 (Hüls) |
| Hydrogenated soybean oil | Sterotex HM NF (Abitec); Dritex S (Abitec) |
| Hydrogenated vegetable oil | Sterotex NF (Abitec); Hydrokote M (Abitec) |
| Hydrogenated cottonseed and castor oil | Sterotex K (Abitec) |
| Partially hydrogenated soybean oil | Hydrokote AP5 (Abitec) |
| Partiaily hydrogenated soy and cottonseed oil | Apex B (Abitec) |
| Glyceryl mono-, di-, tri-behenate | Compritol 888 |
| Glycerol tributyrate | (Sigma) |
| Glyceryl tricaproate | (Sigma) |
| Glyceryl tricaprylate | (Sigma) |
| Glyceryl tricaprate | Captex 1000 (Abitec) |
| Glyceryl triundecanoate | Captex 8227 (Abitec) |
| Glyceryl trilaurate | (Sigma) |
| Glyceryl trimyristate | Dynasan 114 (Hüls) |
| Glyceryl tripalmitate | Dynasan 116 (Hüls) |
| Glyceryl tristearate | Dynasan 118 (Hüls) |
| Glyceryl triarchidate | (Sigma) |
| Glyceryl trimyristoleate | (Sigma) |
| Glyceryl tripalmitoleate | (Sigma) |
| Glyceryl trioleate | (Sigma) |
| Glyceryl trilinoleate | (Sigma) |
| Giyceryl trilinolenate | (Sigma) |
| Glyceryl tricaprylate/caprate | Captex 300 (Abitec); Captex 355 (Abitec); Miglyol 810 (Hüls); Miglyol 812 (Hüls) |
| Glyceryl tricaprylate/caprate/laurate | Captex 350 (Abitec) |
| Glyceryl tricaprylate/caprate/linoleate | Captex 810 (Abitec); Miglyol 818 (Hüls) |
| Glyceryl tricaprylate/caprate/stearate | Softisan 378 (Hüls); (Larodan) |
| Glyceryl tricaprylate/laurate/stearate | (Larodan) |
| Glyceryl 1,2-caprylate-3-linoleate | (Larodan) |
| Glyceryl 1,2-caprate-3-stearate | (Larodan) |
| Glyceryl 1,2-laurate-3-myristate | (Larodan) |
| Glyceryl 1,2-myristate-3-laurate | (Larodan) |
| Glyceryl 1,3-palmitate-2-butyrate | (Larodan) |
| Glyceryl 1,3-stearate-2-caprate | (Larodan) |
| Glyceryl 1,2-linoleate-3-caprylate | (Larodan) |

Fractionated triglycerides, modified triglycerides, synthetic triglycerides, and mixtures of triglycerides are also within the scope of the invention.

Preferred triglycerides include vegetable oils, fish oils, animal fats, hydrogenated vegetable oils, partially hydrogenated vegetable oils, medium and long-chain triglycerides, and structured triglycerides. It should be appreciated that several commercial surfactant compositions contain small to moderate amounts of triglycerides, typically as a result of incomplete reaction of a triglyceride starting material in, for example, a transesterification reaction. Such commercial surfactant compositions, while nominally referred to as "surfactants", may be suitable to provide all or part of the triglyceride component for the compositions of the present invention. Examples of commercial surfactant compositions containing triglycerides include some members of the surfactant families Gelucires (Gattefosse), Maisines (Gattefosse), and Imwitors (Hüls). Specific examples of these compositions are:

Gelucire 44/14 (saturated polyglycolized glycerides)
Gelucire 50/13 (saturated polyglycolized glycerides)
Gelucire 53/10 (saturated polyglycolized glycerides)
Gelucire 33/01 (semi-synthetic triglycerides of $C_8$–$C_{18}$ saturated fatty acids)
Gelucire 39/01 (semi-synthetic glycerides)
other Gelucires, such as 37/06, 43/01, 35/10, 37/02, 46/07, 48/09, 50/02, 62/05, etc.
Maisine 35-I (linoleic glycerides)
Imwitor 742 (capiylic/capric glycerides)

Still other commercial surfactant compositions having significant triglyceride content are known to those skilled in the art. It should be appreciated that such compositions, which contain triglycerides as well as surfactants, may be suitable to provide all or part of the triglyceride component of the compositions of the present invention, as well as all or part of the surfactant component.

4. Substrates

The substrate of the compositions of the present invention can be a powder or a multiparticulate;, such as a granule, a pellet, a bead, a spherule, a beadlet, a microcapsule, a millisphere, a nanocapsule, a nanosphere, a microsphere, a platelet, a minitablet, a tablet or a capsule. A powder constitutes a finely divided (milled, micronized, nanosized, precipitated) form of an active ingredient or additive molecular aggregates or a compound aggregate of multiple components or a physical mixture of aggregates of an active ingredient and/or additives. Such substrates can be formed of various materials known in the art, such as, for example:

Sugars, such as lactose, sucrose or dextrose;
Polysaccharides, such as maltodextrin or dextrates;
Starches;
Cellulosics, such as microcrystalline cellulose or microcrystalline cellulose/sodium carboxymethyl cellulose;
Inorganics, such as dicalcium phosphate, hydroxyapitite, tricalcium phosphate, talc, or titania; and
Polyols, such as mannitol, xylitol, sorbitol or cyclodextrin.

The substrate can also be formed of any of the active ingredients, surfactants, triglycerides or additives described herein. In one particular embodiment, the substrate is a solid form of an additive, an active ingredient, a surfactant, or a triglyceride; a complex of an additive, surfactant or triglyceride and an active ingredient; a coprecipitate of an additive, surfactant or triglyceride and an active ingredient, or a mixture thereof.

It should be emphasized that the substrate need not be a solid material, although often it will be a solid. For example, the encapsulation coat on the substrate may act as a solid "shell" surrounding and encapsulating a liquid or semi-liquid substrate material. Such substrates are also within the scope of the present invention, as it is ultimately the carrier, of which the substrate is a part, which must be a solid.

5. Additives

The solid pharmaceutical compositions of the present invention can optionally include one or more additives, sometimes referred to as excipients. The additives can be contained in an encapsulation coat in compositions which include an encapsulation coat, or can be part of the solid carrier, such as coated to an encapsulation coat, or contained within the components forming the solid carrier. Alternatively, the additives can be contained in the pharmaceutical composition but not part of the solid carrier itself. Specific, non-limiting examples of additives are described below.

Suitable additives are those commonly utilized to facilitate the processes involving the preparation of the solid carrier, the encapsulation coating, or the pharmaceutical dosage form. These processes include agglomeration, air suspension chilling, air suspension drying, balling, coacervation, comminution, compression, pelletization, cryopelletization, extrusion, granulation, homogenization, inclusion complexation, lyophilization, nanoencapsulation, melting, mixing, molding, pan coating, solvent dehydration, sonication, spheronization, spray chilling, spray congealing, spray drying, or other processes known in the art. The additive can also be pre-coated or encapsulated. Appropriate coatings are well known in the art, and are further described in the sections below. Based on the functionality of the additives, examples of the additives are as follows:

5.1. Solubilizers

The pharmaceutical compositions of the present invention can optionally include one or more solubilizers, i.e., additives to increase the solubility of the pharmaceutical active ingredient or other composition components in the solid carrier. Suitable solubilizers for use in the compositions of the present invention include:

- alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives;
- ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);
- amides, such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone;
- esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof;
- and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol monoethyl ether (available from Gattefosse under the trade name Transcutol), and water.

Mixtures of solubilizers are also within the scope of the invention. Except as indicated, these compounds are readily available from standard commercial sources.

Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200–600, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included in compositions of the present invention is not particularly limited. Of course, when such compositions are ultimately administered to a patient, the amount of a given solubilizer is limited to a bioacceptable amount, which is readily determined by one of skill in the art. In some circumstances, it may be advantageous to include amounts of solubilizers far in excess of bioacceptable amounts, for example, to maximize the concentration of active ingredient, with excess solubilizer removed prior to providing the composition to a patient using conventional techniques, such as distillation or evaporation.

5.2. Enzyme Inhibitors

When the active ingredient is subject to enzymatic degradation, the compositions can include an enzyme inhibiting agent. Enzyme inhibiting agents are shown for example, in Bernskop-Schnurch, A., "The use of inhibitory agents to overcome enzymatic barrier to perorally administered therapeutic peptides and proteins", *J. Controlled Release* 52, 1–16 (1998), the disclosure of which is incorporated herein by reference.

Generally, inhibitory agents can be divided into the following classes:

- Inhibitors that are not based on amino acids, such as P-aminobenzamidine, FK-448, camostat mesylate, sodium glycocholate;
- Amino acids and modified amino acids, such as aminoboronic acid derivatives and n-acetylcysteine;
- Peptides and modified peptides, such as bacitracin, phosphinic acid dipeptide derivatives, pepstain, antipain, leupeptin, chymostatin, clastatin, bestatin, phosphoramindon, puromycin, cytochalasin potatocarboxy peptidase inhibitor, and amastatin;
- Polypeptide protease inhibitors, such as aprotinin (bovine pancreatic trypsin inhibitor), Bowman-Birk inhibitor and soybean trypsin inhibitor, chicken egg white trypsin inhibitor, chicken ovoinhibitor, and human pancreatic trypsin inhibitor. Complexing agents, such as EDTA, ERRTA, 1,10-phenanthroline and hydroxychinoline; and
- Mucoadhesive polymers and polymer-inhibitor conjugates, such as polyacrylate derivatives, chitosan, cellulosics, chitosan-EDTA, chitosan-EDTA-antipain, polyacrylic acid-bacitracin, carboxymethyl cellulose-pepstatin, polyacrylic acid-Bwoman-Birk inhibitor.

The choice and levels of the enzyme inhibitor are based on toxicity, specificity of the proteases and the potency of the inhibition. The inhibitor can be suspended or solubilized in the composition preconcentrate, or added to the aqueous diluent or as a beverage.

Without wishing to be bound by theory, it is believed that an inhibitor can function solely or in combination as:

- a competitive inhibitor, by binding at the substrate binding site of the enzyme, thereby preventing the access to the substrate; examples of inhibitors believed to operate by this mechanism are antipain, elastatinal and the Bowman Birk inhibitor;
- a non-competitive inhibitor which can be simultaneously bound to the enzyme site along with the substrate, as their binding sites are not identical; and/or
- a complexing agent due to loss in enzymatic activity caused by deprivation of essential metal ions out of the enzyme structure.

5.3. Other Additives

Other additives conventionally used in pharmaceutical compositions can be included, and these additives are well known in the art. Such additives include:

- anti-adherents (anti-sticking agents, glidants, flow promoters, lubricants) such as talc, magnesium stearate, fumed silica (Carbosil, Aerosil), micronized silica (Syloid No. FP 244, Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate;

anticoagulants, such as acetylated monoglycerides;

antifoaming agents, such as long-chain alcohols and silicone derivatives;

antioxidants, such as BHT, BHA, gallic acid, propyl gallate, ascorbic acid, ascorbyl palmitate, 4-hydroxymethyl-2,6-di-tert-butyl phenol, and tocopherol;

binders (adhesives), i.e., agents that impart cohesive properties to powdered materials through particle-particle bonding, such as matrix binders (dry starch, dry sugars), film binders (PVP, starch paste, celluloses, bentonite, sucrose), and chemical binders (polymeric cellulose derivatives, such as carboxy methyl cellulose, HPC and HPMC; sugar syrups; corn syrup; water soluble polysaccharides such as acacia, tragacanth, guar and alginates; gelatin; gelatin hydrolysate; agar; sucrose; dextrose; and non-cellulosic binders, such as PVP, PEG, vinyl pyrrolidone copolymers, pregelatinized starch, sorbitol, and glucose);

bufferants, where the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and where the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid;

chelating agents, such as EDTA and EDTA salts;

coagulants, such as alginates;

colorants or opaquants, such as titanium dioxide, food dyes, lakes, natural vegetable colorants, iron oxides, silicates, sulfates, magnesium hydroxide and aluminum hydroxide;

coolants, such as halogenated hydrocarbons (e.g., trichloroethane, trichloroethylene, dichloromethane, fluorotrichloromethane), diethylether and liquid nitrogen;

cryoprotectants, such as trehelose, phosphates, citric acid, tartaric acid, gelatin, dextran and mannitol;

diluents or fillers, such as lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose, disintegrants or super disintegrants, such as croscarmellose sodium, starch, starch derivatives, clays, gums, cellulose, cellulose derivatives, alginates, crosslinked polyvinypyrrolidone, sodium starch glycolate and microcrystalline cellulose;

hydrogen bonding agents, such as magnesium oxide;

flavorants or desensitizers, such as spray-dried flavors, essential oils and ethyl vanillin;

ion-exchange resins, such as styrene/divinyl benzene copolymers, and quaternary ammonium compounds;

plasticizers, such as polyethylene glycol, citrate esters (e.g., triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl seccate;

preservatives, such as ascorbic acid, boric acid, sorbic acid, benzoic acid, and salts thereof, parabens, phenols, benzyl alcohol, and quaternary ammonium compounds;

solvents, such as alcohols, ketones, esters, chlorinated hydrocarbons and water;

sweeteners, including natural sweeteners such as maltose, sucrose, glucose, sorbitol, glycerin and dextrins, and artificial sweeteners, such as aspartame, saccharine and saccharine salts; and thickeners (viscosity modifiers, thickening agents), such as sugars, polyvinylpyrrolidone, cellulosics, polymers and alginates.

Additives can also be materials such as proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum arabic); spermaceti; natural or synthetic waxes; carnuaba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based shellacs (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate trimellitate, carboxymethylethyl cellulose, hydroxypropylmethyl cellulose phthalate); inorganics, such as dicalcium phosphate, hydroxyapitite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar.

It should be appreciated that there is considerable overlap between the above-listed additives in common usage, since a given additive is often classified differently by different practitioners in the field, or is commonly used for any of several different functions. Thus, the above-listed additives should be taken as merely exemplary, and not limiting, of the types of additives that can be included in compositions of the present invention. The amounts of such additives can be readily determined by one skilled in the art, according to the particular properties desired.

6. Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery, although oral delivery is presently preferred.

The pharmaceutical composition and/or the solid carrier particles can be coated with one or more enteric coatings, seal coatings, film coatings, barrier coatings, compress. coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be effected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided:

Seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coating: The term "extended release coating" as used herein means a coating designed to effect delivery over an extended period of time. Preferably, the extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coating; The term "enteric coating" as used herein relates to a mixture of pharmaceutically acceptable excipients which is applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties:

1. resistance to dissolution and disintegration in the stomach;
2. impermeability to gastric fluids and drug/carrier/enzyme while in the stomach;
3. ability to dissolve or disintegrate rapidly at the target intestine site;
4. physical and chemical stability during storage;
5. non-toxicity;
6. easy application as a coating (substrate friendly); and
7. economical practicality.

Dosage forms of the compositions of the present invention can also be formulated as enteric coated delayed release oral dosage forms, i.e., as an oral dosage form of a pharmaceutical composition as described herein which utilizes an enteric coating to effect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. The preferred polymers for use in the present invention are anionic carboxylic polymers. The more preferred polymers and compatible mixtures thereof, and some of their properties, include, but are not limited to:

Shellac, also called purified lac, a refined product obtained from the, resinous secretion of an insect. This coating dissolves in media of pH>7.

Acrylic polymers (preferred). The performance of acrylic polymers (primarily their solubility in biological fluids) can vary based on the degree and type of substitution. Examples of suitable acrylic polymers include methacrylic acid copolymers and ammonio methacrylate copolymers. The Eudragit series E, L, S, RL, RS and NE (Rohm Pharma) are available as solubilized in organic solvent, aqueous dispersion, or dry powders. The Eudragit series RL ,NE, and RS are insoluble in the gastrointestinal tract but are permeable and are used primarily for extended release. The Eudragit series E dissolve in the stomach. The Eudragit series L, L-30D and S are insoluble in stomach and dissolve in the intestine.

Cellulose Derivatives (also preferred). Examples of suitable cellulose derivatives are:

ethyl cellulose;

reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 $\mu$m. Other components in Aquateric can include pluronics, Tweens, and acetylated monoglycerides;

cellulose acetate trimellitate (Eastman);

methylcellulose (Pharmacoat, Methocel);

hydroxypropyl methyl cellulose phthalate (HPMCP). The performance can vary based on the degree and type of substitution. HP-50, HP-55, HP-55S, HP-55F grades are suitable;

hydroxypropyl methyl cellulose succinate (HPMCS; AQOAT (Shin Etsu)).

The performance can vary based on the degree and type of substitution. Suitable grades include AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids; and Cotteric (by Colorcon).

Combinations of the above materials can also be used.

The coating can, and usually does, contain a plasticizer and possibly other coating excipients such as colorants, talc, and/or magnesium stearate, which are well known in the art. Suitable plasticizers include: triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10–25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the lower intestinal tract is reached.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

A particularly suitable methacrylic copolymer is Eudragit L.RTM, particularly L-30D.RTM and Eudragit 100-55.RTM, manufactured by Rohm Pharma, Germany. In Eudragit L-30 D.RTM, the ratio of free carboxyl groups to ester groups is approximately 1:1. Further, the copolymer is known to be insoluble in gastrointestinal fluids having pH below 5.5, generally 1.5–5.5, i.e., the pH generally present in the fluid of the upper gastrointestinal tract, but readily soluble or partially soluble at pH above 5.5, i.e., the pH generally present in the fluid of lower gastrointestinal tract.

Another methacrylic acid polymer which is suitable for use in coating the composition or solid carrier which can be employed in the compositions and methods described herein, either alone or in combination with other coatings, is Eudragit S.RTM, manufactured by Rohm Pharma, Germany. Eudragit S.RTM. differs from Eudragit L-30-D.RTM only insofar as the ratio of free carboxyl groups to ester groups is approximately 1:2. Eudragit S.RTM is insoluble at pH below 5.5, but unlike Eudragit L-30-D.RTM, is poorly soluble in gastrointestinal fluids having pH of 5.5–7.0, such as is present in the small intestine media. This copolymer is soluble at pH 7.0 and above, i.e., the pH generally found in the colon. Eudragit S.RTM can be used alone as a coating to provide delivery of beginning at the large intestine via a delayed release mechanism. In addition, Eudragit S.RTM, being poorly soluble in intestinal fluids below pH 7, can be used in combination with Eudragit L-30-D.RTM, soluble in intestinal fluids above pH 5.5, in order to effect a delayed release composition. The more Eudragit L-30 D. RTM used the more proximal realease and delivery begins, and the more Eudragit S.RTM used, the more distal release and delivery begins Both Eudragit L-30-D-RTM and Eudragit S.RTM can be substituted with other pharmaceutically acceptable polymers with similar pH solubility characteristics.

Preferred materials include shellac, acrylic polymers, cellulosic derivatives, polyvinyl acetate phthalate, and mixtures thereof. More preferred materials include Eudragit series E, L, S, RL, RS, NE, L.RTM, L300.RTM, S.RTM, 100-55RTM, cellulose acetate phthalate, Aquateric, cellulose acetate trimellitate, ethyl cellulose, hydroxypropyl methyl cellulose phthalate, hydroxypropyl methyl cellulose succinate, poly vinyl acetate phthalate, and Cotteric. Most preferred materials include Eudragit series L.RTM, L300.RTM, S.RTM, L100-55RTM, cellulose acetate phthalate, Aquateric, ethyl cellulose, hydroxypropyl methyl cellulose phthalate, hydroxypropyl methyl cellulose succinate, poly vinyl acetate phthalate, and Cotteric.

Extended release and targeted delayed release coatings for dosage forms of the compositions of the present invention are described more completely in U.S. Pat. Nos. 5,622,721 and 5,686,105, the disclosures of which are incorporated herein by reference in their entirety.

Fast-Disintegrating Coatings for Immediate Release: Immediate release coating of solid carriers is commonly used to improve product elegance as well as for a moisture barrier, and taste and odor masking. Rapid breakdown of the film in gastric media is important, leading to effective disintegration and dissolution. Eudragit RD100 (Rohm) is an example of such a coating. It is a combination of a water insoluble cationic methacrylate copolymer with a water soluble cellulose ether. In powder form, it is readily dispensible into an easily sprayable suspension that dries to leave a smooth film. Such films rapidly disintegrate in aqueous media at a rate that is independent of pH and film thickness.

7. Processes

The compositions of the present invention can be prepared by a variety of processes to apply an encapsulation coat onto a substrate or to form a substrate-free solid carrier such as a multiparticulate or a powder. The commonly utilized coating and pelletization processes include balling, spheronization, extrusion, spray congealing, spray drying, pan coating, fluidized bed coating, melt extrusion, crystallization, cryopelletization, nanoencapsulation, coacervation, etc. It is also clear to one skilled in the art that appropriate additives can also be introduced to the composition or during the processes to facilitate the preparation of the solid carrier or the dosage forms, depending on the need of the individual process.

A coating process frequently involves spraying a coating solution onto a substrate. The coating solution can be a molten solution of the encapsulation coat composition free of a dispersing, medium. The coating solution can also be prepared by solubilizing or suspending the composition of the encapsulation coat in an aqueous medium, an organic solvent, a supercritical fluid, or a mixture thereof. At the end of the coating process, the residual dispersing medium can be further removed to a desirable level utilizing appropriate drying processes, such as vacuum evaporation, heating, freeze drying, etc.

A pelletization process typically involves preparing a molten solution of the composition of the solid carrier or a dispersion of the composition of the solid carrier solubilized or suspended in an aqueous medium, an organic solvent, a supercritical fluid, or a mixture thereof. Such solution or dispersion is then passed through a certain opening to achieve the desired shape, size, and other properties. Similarly, appropriate drying processes can be adopted to control the level of the residual dispersing medium, if necessary.

The processes described above, the combination of the processes, or the modification of the processes are well know in the art. Some of the processes are briefly described herein for reference.

Balling, Spheronization or Extrusion

In a broad sense, pellets are very much like granules and bead; the techniques for producing pellets can also produce granules, beads, etc. Pellets, granules or beads are formed with the aid of a pelletizer, spheronizer or extruder. The pelletizer, spheronizer or extruder is able to form approximately spherical bodies from a mass of finely divided particles continuously, by a rolling or tumbling action on a flat or curved surface with the addition of a liquid.

Pelletizers can be classified based on the angle of their axis as horizontal drum or inclined dish pelletizers. Rotary fluidized granulators can also be used for pelletization. A standard fluidized drier bowl can be replaced with a rotating plate as an air distributor. For granulation, a binder liquid is sprayed from via one or two binary nozzles located axially to the rotational movement of the powder bed. This operation results in rounding of the granules to approximately spherical pellets. Such balling or agitation techniques can be influenced by operating conditions, such as bridging/binding liquid requirements, residence time of the material in the pelletizer, speed and angle of inclination of the pelletizer, amount of material fed to the pelletizer, choice and levels of binder, etc. One skilled in the art can readily adjust such factors to produce a satisfactory product.

The components of the invention can also be self binding. Liquid components can be pelletized with an the aid of suitable solidifying, binding or thickening agents.

Similarly, the choice of an appropriate binder for a given application is readily determined by one skilled in the art. At a minimum, the binder must be capable of wetting the surfaces of the particle being pelletized or granulated. Binders must have sufficient wet strength to allow agglomerates to be handled, and sufficient dry strength to make them suitable for their intended purposes. Each process, however, makes use of a different system of forces and may require a different agglomerate strength. The final selection of the binder should be made on the basis of the type of equipment that is used. The size and size distribution of pellets, bulk density, strength and flow properties also affect the performance of the pellets, and these properties can be adjusted by one skilled in the art by the inclusion of additives, choice of equipment, and processing conditions.

Extrusion

Extrusion is a well-known method of applying pressure to a damp or melted composition until it flows through an orifice or a defined opening. The extrudable length varies with the physical characteristics of the material to be extruded, the method of extrusion, and the process of manipulation of the particles after extrusion. Various types of extrusion devices can be employed, such as screw, sieve and basket, roll, and ram extruders.

Encapsulation by Extrusion: In this method, the lipid composition in the form of an emulsion is added to a low moisture melt of low maltodextrin, or sugar, or modified edible starch, mixed and extruded into a cold bath. The solidified composition can be further ground down. Optionally, centrifugal extrusion can be utilized for efficiency.

Melt Extrusion: Components of the invention can be melted and extruded with a continuous, solvent free extrusion process, with or without inclusion of additives. Such a process is well-established and well-known to skilled practitioners in the art.

Spheronization

Spheronization is the process of converting material into spheres, the shape with the lowest surface area to volume ratio. Spheronization typically begins with damp extruded particles. The extruded particles are broken into uniform lengths instantaneously and gradually transformed into spherical shapes. In addition, powdered raw materials, which require addition of either liquid or material from a mixer, can be processed in an air-assisted spheronizer.

Spray Congealing

Spray congealing is method that is generally used in changing the structure of the materials, to obtain free flowing powders from liquids and to provide pellets ranging in size from about 0.25 to 2.0 mm. Spray congealing is process in which a substance of interest is allowed to melt, disperse, or dissolve in a hot melt of other additives, and is then sprayed into an air chamber wherein the temperature is below the melting point of the formulation components, to provide spherical congealed pellets. The air removes the latent heat of fusion. The temperature of the cooled air used depends on the freezing point of the product. The particles are held together by solid bonds formed from the congealed melts. Due to the absence of solvent evaporation in most spray congealing processes, the particles are generally non porous and strong, and remain intact upon agitation. The characteristics of the final congealed product depend in part on the properties of the additives used. The rate of feeding and inlet/outlet temperatures are adjusted to ensure congealing of the atomized liquid droplet. The feed should have adequate viscosity to ensure homogeneity. The conversion of molten feed into powder is a single, continuous step. Proper atomization and a controlled cooling rate are critical to obtain high surface area, uniform and homogeneous congealed pellets. Adjustment of these parameters is readily achieved by one skilled in the art.

The spray congealing method is particularly suitable for heat labile substances, since ambient temperature is used to dry, and for moisture sensitive substances, since non-aqueous compositions can be utilized. Spray congealing is similar to spray drying, except that no solvent is utilized. Spray congealing is a uniform and rapid process, and is completed before the product comes in contact with any equipment surface. Most additives that are solid at room temperature and melt without decomposition are suitable for this method.

Conventional spray dryers operating with cool inlet air have been used for spray congealing. Several methods of atomization of molten mass can be employed, such as pressure, or pneumatic or centrifugal atomization. For persons skilled in the spray congealing art, it is well known that several formulation aspects, such as matrix materials, viscosity, and processing factors, such as temperature, atomization and cooling rate affect the quality (morphology, particle size distribution, polymophism and dissolution characteristics) of spray congealed pellets. The spray congealed particles may be used in tablet granulation form, encapsulation form, or can be incorporated into a liquid suspension form.

Solvent Dehydration (Spray Drying)

For compositions that are oily in nature, the spray drying technique is commonly employed. The oily material is commonly mixed with a polymeric material, such as gelatin, vegetable gum, modified starch, dextrin, or other appropriate additives. An emulsifier is added, if needed, to form an oil-in-water emulsion. The emulsion is atomized into a column of heated air in a drying chamber, resulting in rapid evaporation of water. Alternatively, the emulsion is atomized directly into a polar solvent, such as isopropanol, ethanol, glycerol or polyglycols, to dehydrate the aerosolized particle. This method is particularly suitable for compositions containing lipophilic actives or additives that result in lipophilic cores. Spray drying/solvent dehydration can also be applied to hydrophilic active ingredients or additives to form an oil in water emulsion which is spray dried. This results in a homogenous solid composition. Furthermore, water or organic solvent based formulations can be spray dried by using inert process gas, such as nitrogen, argon and the like.

Crystallization

Components of the present invention can be dissolved in appropriate solvents and subjected to spherical crystallization techniques well-known in the art.

Nanoencapsulation

Nanoencapsulation involves solubilizing an aqueous solution of an active ingredient and other components in a weakly polar vehicle. Micelles are formed with the active in an organic outer phase. Then, an amphiphilic monomer is added to the lipophilic external phase. The mixed micelles thus formed are then polymerized with the aid of a suitable procedure, such as UV or gamma radiation, heat, or chemical agents. The hardened solidified micelles are made to undergo phase exchange by replacing an outer lipophilic vehicle by water. By selecting appropriate monomers, networking agents and auxiliary materials, nanocapsules as small as 80 to 250 nm can be prepared.

Supercritical Fluid Processes

Components of the present invention can be dispersed in a supercritical fluid and crystallized as needed. Current techniques involving supercritical fluids include precipitation by rapid expansion of supercritical solutions, gas anti-solvent processes, and precipitation from gas saturated solutions.

Coacervation

Coacervation is a transfer of macromolecules with film properties from a solvated state in a coacervation phase into a phase in which there is a film around each particle. The coacervation method involves dispersing the composition in a dispersion of a polymeric colloid, such as gelatin alginate, and shock treating the mixture with temperature or pH, etc., to generate a two-phase system. The desired phase is then hardened with a cross-linking agent, such as glutaraldehyde.

Cryopelletization

The cryopelletization procedure allows conversion of a molten mass, aqueous solution or suspension into solid, bead-like particles. The molten mass solutions or suspensions are dripped by means of an appropriately designed device into liquid nitrogen. The production of small drops and liquid nitrogen cooling permit very rapid and uniform freezing of the material processed. The pellets are further dried in conventional freeze dryers. Cryopelletization can also be carried out under aseptic conditions for sterile processing. The most critical step producing spherical particles by globulization is the droplet formation. Droplet formation is influenced by formulation related variables, such as the nature of the active ingredient and additives, viscosity, total solid content, surface tension, etc. Extra care must be undertaken with processing of suspensions to ensure homogeneity. In addition, equipment design and processing variable also play an important role. One skilled in the art can readily balance the various factors to produce a satisfactory product. Enteric matrix pellets can be formed that include polyacrylic acid (e.g. Carbopol) with a high molecular weight polyethylene (such as PEG-20,000).

Other processes suitable for producing solid compositions of the pharmaceutical compositions of the present invention include extrusion and spray chilling. These processes are described in detail in U.S. Pat. Nos. 5,965,161 and 5,539,000 respectively, the disclosures of which are incorporated herein by reference.

For processing of encapsulated compositions, various methods can be used. The term "microencapsulation" applies to enclosure or encasement in microcapsules. Microencapsulation is a means of applying coatings to small particles of solids or droplets of liquids and dispersions. The terms "coated", "protected" or "layered" are commonly used interchangeably with the term "encapsulated". All of these terms can be used to refer to practically any core material that is encased or enclosed in an outer shell. Typical equipment used to apply coating includes a conventional pan (Pellegrini; Italy), a modified perforated pan (multicoater, Thomas Eng., Ill.) or a Wurster coater in a Glatt powder doater/granulator (Glatt Airtechniques).

Solvent Based Solution Coating

Solvent-based coating is when the components of the invention are solubilized and/or dispersed in a solvent. The solvent can be aqueous. When the solvent is aqueous-based, the components can be emulsified with an appropriate emulsifier, organic solvent, or a supercritical fluid. Solvents with a lower melting point than water and higher evaporation numbers are preferred. Solvent mixtures with other organic solvents or water are often employed to get appropriate viscosity and component solubilization. Typical solvents include ethanol, methanol, isopropanol, acetone, dichloromethane, trichloromethane and ethyl acetate. Appropriate polymers can also be added as needed. Cellulosic derivatives and polymethacrylates are particularly suitable additives for organic solvent coating. Dissolution and solubilization of the components is facilitated by rigorous stirring or heating. Plasticizers may be also be added to stimulate dissolution. Colorants and antisticking agents can be employed as needed.

Substrate surface area, shape, porosity and stability are important determinants of good coating. Spherical particles are preferred, and these may be produced through spheronization or a spherical crystallization process. Crystals or compact granules from dry compaction or extrusion processes, often available commercially, serve as good substrates.

Encapsulation can be conducted by traditional pan coating or fluidized bed techniques. Several process (air supply, temperature, spray rate, spray system, powder feed, attrition) and formulation factors determine the quality of the end product, and one skilled in the art can readily adjust such parameters as needed.

Air suspension in a rotary fluidized bed granulator can used to deposit the encapsulation coat on to a substrate, thus allowing a high rate of drug application with low drug loss. Furthermore, both aqueous and organic solvents can be used. The Wurster process, an air suspension technique, is more suitable for encapsulations involving very fine powders.

Solvent-Free Coating

This process entails using coating materials that can be applied in a molten state. The selection of proper coating -materials depends on melting point, melting point range and the viscosity in the liquid state. A fluidized bed is ideal for molten coatings of substrates that range from about 100 microns to about 2000 microns in size. Fluidized bed coating, spraying molten materials, involves achieving a proper balance of process parameters that allow proper encapsulation to occur. Substrate particles that are suspended and separated from each other by the fluidization air enter a zone of finely atomized coating liquid. Coating occurs as the liquid droplets, which are substantially smaller in size than substrate, impact the particles, spread, and solidify. Multiple layers can be coated, and the completion of spraying is followed by a product stabilization or cooling step. Some critical success parameters include bed temperature, atomization, atomization fluid temperature, or droplet size, spray type, spray rate, rate of coating droplet solidification on particle surfaces, particle size, shape, etc. Inert materials such as sodium chloride, citric acid, potassium chloride can serve as substrates. One skilled in the art can readily adjust such parameters to achieve a satisfactory product.

The processes described above are suitable for treating substrate-based compositions or non-substrate-based compositions of the present invention. Thus, in one embodiment, pharmaceutical compositions of the present invention do not include a seed particle, such as a conventional drug or other additive aggregate starch or sugar bead. Instead, the compositions are processed, and the components are chosen, such that a solid composition is formed without the need to coat the composition onto a substrate bead. Such compositions can be in the form of beadlets, beads, granules, pellets, etc., that have an approximately homogenous distribution of active ingredient, surfactant, triglyceride and/or additives. These compositions can be produced by means of balling in pelletizers or fluid bed granulators, and compaction or extrusion/spheronization. In addition, these compositions can be produced using solvent-free spray congealing processes or dropping (globulization) methods. Dropping procedures involve conversion of aqueous solutions or suspensions to a solid form. Congealing of the liquid droplets in cooling baths can aided by a chemical reaction (e.g., insoluble salt or complex formation), a sol/gel transition, or by freezing in a coolant bath of liquid nitrogen or halogenated hydrocarbons.

8. Specific Formulations

In one embodiment, the solid pharmaceutical composition includes a solid carrier, the solid carrier including a substrate and an encapsulation coat on the substrate. The encapsulation coat includes at least one ionic or non-ionic hydrophilic surfactant. Optionally, the encapsulation coat can include a pharmaceutical active ingredient, a lipophilic component such as a lipophilic surfactant or a triglyceride, or both a pharmaceutical active ingredient and a lipophilic component.

Prior art has used surfactants in formulating coated bead compositions to provide a wetting function, to enable hydrophobic drugs to properly adhere to beads and/or watersoluble binders. For example, U.S. Pat. No. 4,717,569 to Harrison et al. discloses coated bead compositions of hydrophobic steroid compounds wetted by a hydrophilic surfactant and adhered to the beads by a water-soluble binder. The steroid compound is present as finely divided particles, held to the beads by the binder. The present inventors have surprisingly found that proper choice of surfactants and other components allows compositions to be prepared with a wide variety of hydrophilic or hydrophobic active ingredients. For example, while the Harrison reference discloses the use of surfactants as wetting agents, the present inventors have found that surfactants at higher levels, i.e., in amounts far in excess of the amounts necessary or appropriate for a wetting function, enable a pharmaceutical active ingredient to be fully or at least partially solubilized in the encapsulation coating material itself, rather than merely physically bound in a binder matrix. In fact, while binders can optionally be used in the compositions of the present invention, the higher surfactant concentrations of the present invention, i.e., solubilizing amounts, obviate the need for binders and render them optional instead of necessary.

The amount of hydrophilic surfactant used in this embodiment can be adjusted so as to at least partially solubilize the pharmaceutical active ingredient, with the optional lipophilic surfactants and triglycerides chosen to further increase the pharmaceutical active ingredient's solubility.

A further advantage believed to accrue from the pharmaceutical compositions of the present invention is that upon administration of the composition to a patient, the high levels of surfactants and other components present in the composition facilitate the rapid solubilization of the pharmaceutical active ingredient. Thus, while the prior art composition of Harrison contains a drug in a form which requires further solubilization in vivo, such as by emulsification and micellization in the gastrointestinal tract, the active ingredient in compositions of the present invention is at least partially solubilized in the composition itself, and is further provided with surfactants and other components in the composition to facilitate rapid dispersion (emulsification/micellization) and sustained solubilization of the active ingredient upon administration.

It should be noted that in this embodiment, the encapsulation coat can alternatively be formulated without an active ingredient. In this aspect, an active ingredient can be provided in the composition itself but not in the encapsulation coat, if desired. While not presently preferred, such a formulation delivers the active ingredient to the patient along with the surfactants and other components to facilitate dispersion (emulsification/micellization), thus still providing more rapid active ingredient presentation to the absorption site. Alternatively, the active ingredient can be administered in a separate dosage form, including a conventional dosage form, prior to, concurrently with, or subsequent to administration of the present compositions, to achieve similar advantages.

The optional lipophilic surfactant and triglycerides can be used as desired to further enhance solubilization of the active ingredient, or to promote dispersion (emulsification/micellization) in vivo, or to promote in vivo absorption at the absorption site.

For more hydrophilic active ingredients, the materials of the encapsulation coat provides components to promote efficient transport of the active ingredient across the barrier membrane to promote more effective absorption. For these active ingredients, it is preferable to include a lipophilic component in the encapsulation coat.

In another embodiment, the solid pharmaceutical composition includes a solid carrier, the solid carrier, including a substrate and an encapsulation coat on the substrate. The encapsulation coat includes a lipophilic component, such as a lipophilic surfactant or a triglyceride. Optionally, the encapsulation coat can include a pharmaceutical active ingredient, an ionic or non-ionic hydrophilic surfactant, or both a pharmaceutical active ingredient and a hydrophilic surfactant. In this embodiment, the lipophilic surfactant or triglyceride can be present in amounts to enable at least partial solubilization of an active ingredient in the encapsulation coat, in the composition, or separately administered.

In another embodiment, the solid pharmaceutical composition effectively presents a lipophilic component with or without an active ingredient to help promote absorption of a hydrophilic active.

In another embodiment, the solid pharmaceutical composition includes a solid carrier, the solid carrier including a substrate and an encapsulation coat on the substrate. The encapsulation coat includes a pharmaceutical active ingredient and an ionic or non-ionic hydrophilic surfactant; a pharmaceutical active ingredient and a lipophilic component such as a lipophilic surfactant or a triglyceride; or a pharmaceutical active ingredient and both a hydrophilic surfactant and a lipophilic component.

In another embodiment, the solid pharmaceutical composition includes a solid, carrier, wherein the solid carrier is formed of at least two components selected from the group consisting of pharmaceutical active ingredients; ionic or non-ionic hydrophilic surfactants; and lipophilic components such as lipophilic surfactants and triglycerides.

In this embodiment, the solid pharmaceutical composition is formulated without the need for a substrate seed particle. The active ingredient, surfactants and triglycerides in the chosen combination are processed, with appropriate excipients if necessary, to form solid carriers in the absence of a seed substrate. Preferably, the components are chosen to at least partially solubilize the active ingredient, as described above.

9. Methods

The present invention also provides methods of using the above-described pharmaceutical composition. In one aspect, the present invention provides a method of treating a patient with a pharmaceutical active ingredient, the method including the steps of providing a dosage form of a pharmaceutical composition as described above, including an active ingredient, and administering the dosage form to the patient. The patient can be an animal, preferably a mammal, and more preferably a human.

In another aspect, the present invention provides a method including the steps of providing a dosage form of a pharmaceutical composition as described above, providing a dosage form of a pharmaceutical active ingredient, and administering the dosage forms to the patient. This method is advantageous when all or part of the active ingredient or an additional active ingredient is to be administered to the patient in a separate dosage form prior to, concurrently with, or subsequent to administration of the pharmaceutical composition.

In another aspect, the present invention provides a method of improving the palatability and/or masking the taste of a pharmaceutical active ingredient, by providing the active ingredient in a pharmaceutical composition as described above. Since the active ingredient is encapsulated in a lipid coat, it will not instantaneously dissolve in the mouth, but will instead dissolve in a region past the oral cavity, thereby substantially avoiding or at least reducing undesirable contact between the active ingredient and the mouth.

In another aspect of the invention, the compositions enable gastric resistance or acid degradation reduction of the active ingredient.

In another aspect of the invention, the solid carrier improves the chemical stability of the active ingredient.

In another aspect of the invention, the solid carrier protects the upper gastrointestinal tract from the adverse effects of the active ingredient.

In another aspect, the present invention provides a method of improving the dissolution and/or absorption of a pharmaceutical active ingredient, by administering the active ingredient in a composition as described above, or co-administering the active ingredient with a composition as described above.

EXAMPLES

Example 1

Preparation of Coated Beads

Compositions according to the present invention were prepared as follows. The specific components used are detailed in Examples 2–5.

A spraying solution of the coating materials was prepared by dissolving the desired amount of the active ingredient and mixing with the hydrophilic and/or lipophilic surfactants in an organic solvent or a mixture of organic solvents. The organic solvent used for the coating solution was a mixture of methylene chloride and isopropyl alcohol in a 3:1 to 1:1 weight ratio.

Commercially available sugar beads (30/35 mesh size) were coated in a conventional coating pan having a spray gun (Campbell Hausfield, DH 7500) with a nozzle diameter of 1.2 mm and an air pressure of 25 psi. The bed temperature was maintained at approximately 32° C. during the spraying process. Appropriate amounts of talc were sprinkled on the beads during the spraying process to reduce the agglomeration of coated beads. When the spraying process was completed, the coated beads were allowed to cool to room temperature. The coated beads were then dried under vacuum to minimize residual solvent levels. The dried, coated beads were then sieved and collected.

Example 2

Composition I

A pharmaceutical composition was prepared according to the method of Example 1, having a substrate particle, an active ingredient (glyburide), and a mixture of a hydrophilic surfactant (PEG-40 stearate) and a lipophilic surfactant (glycerol monolaurate). The components and their amounts were as follows:

| Component | Weight (g) | % (w/w) |
|---|---|---|
| Glyburide | 1 | 0.8 |
| PEG-40 stearate | 33 | 25.2 |
| Glycerol monolaurate | 17 | 13.0 |
| Non-pareil seed (30/35 mesh) | 80 | 61.1 |

Example 3

Composition II

A pharmaceutical composition was prepared according to the method of Example 1, having a substrate particle, an active ingredient (progesterone), a mixture of a hydrophilic surfactant (Solulan C-24) and two lipophilic components (deoxycholic acid and distilled monoglycerides). The components and their amounts were as follows:

| Component | Weight (g) | % (w/w) |
|---|---|---|
| Progesterone | 12 | 8.6 |
| Solulan C-24 (Amerchol)* | 32 | 22.9 |
| Distilled monoglycerides | 8 | 5.7 |
| Deoxycholic acid | 8 | 5.7 |
| Non-pareil seed (30/35 mesh) | 80 | 57.1 |

*PEG-24 cholesterol ether

Example 4

Composition III

A pharmaceutical composition was prepared according to the method of Example 1, having a substrate particle, an active ingredient (itraconazole), a mixture of non-ionic hydrophilic surfactants (Cremophor RH-40 and PEG-150 monostearate), an ionic hydrophilic surfactant (sodium taurocholate) and a lipophilic surfactant (glycerol monolaurate). The components and their amounts were as follows:

| Component | Weight (g) | % (w/w) |
|---|---|---|
| Itraconazole | 20 | 9.7 |
| Cremophor RH-40 (BASF)* | 25 | 12.1 |
| Glycerol monolaurate | 10 | 4.8 |
| Sodium taurocholate | 5 | 2.4 |
| PEG-150 monostearate | 27 | 13.0 |
| Non-pareil seed (30/35 mesh) | 120 | 58.0 |

*PEG-40 hydrogenated castor oil

Example 5

Composition IV

A pharmaceutical composition was prepared according to the method of Example 1, having a substrate particle, an active ingredient (omeprazole), a mixture of a two hydrophilic surfactants (PEG-150 monostearate and PEG-40 monostearate), and a triglyceride-containing lipophilic component (Maisine 35-1). The components and their amounts were as follows:

| Component | Weight (g) | % (w/w) |
|---|---|---|
| Omeprazole | 16 | 8.8 |
| PEG-150 monostearate | 50.4 | 27.8 |
| PEG-40 monostearate | 25.2 | 13.9 |
| Maisine 35-1 (Gattefosse)* | 8.4 | 4.6 |
| Magnesium carbonate | 1.6 | 0.9 |
| Non-pareil seed (30/35 mesh) | 80 | 44.1 |

*linoleic glycerides

Example 6

Seal Coating

The dried, coated beads of Example 3 were further seal coated by a polymer layer. The seal coating polymer layer was applied to the progesterone-coated beads in a Uni-Glatt fluid bed coater. Polyvinylpyrrolidone (PVP-K30) was dissolved in isopropyl alcohol to form a 5% w/w solution. This seal coating solution was sprayed onto the coated beads with a Wurster bottom spray insert. The inlet and outlet air temperature were maintained at 30 and 40° C., respectively. When the spraying process was complete, the beads were further dried by supplying dry air at 50–55° C. for 5–15 minutes. The seal coated beads were then allowed to cool in the apparatus by supplying dry air at 20–25° C. for 5–15 minutes. The dried, seal coated beads were collected and stored in a container.

Example 7

Protective Coating

The dried, coated beads of Example 5 were further coated with a protective polymer layer. The protective coating was applied to the omeprazole coated beads by spraying with a hydroxypropyl methylcellulose (HPMC) solution. The protective coating HPMC solution was prepared by dissolving 6 grams of HPMC in ethanol. To this solution, methylene chloride was added followed by 2 mL of triethylcitrate as a plasticizer and 1 g of talc the HPMC solution was sprayed on the beads as described in Example 6, and the protective coated beads were then dried and collected.

Example 8

Enteric Coating

The dried, coated beads of Example 5 were further coated with an enteric coating layer. The enteric layer was applied to the omeprazole coated beads by spraying a Eudragit L100 solution. Eudragit L100 is an acrylate polymer commercially available from Rohm Pharma. The spraying solution was prepared by dispersing 15 g of Eudragit L100 in 200 mL of ethanol to give a clear solution. To this solution, 4 g of triethyl citrate was then added as a plasticizer. 2 grams of purified talc was also added to the solution. The solution was then sprayed onto the beads, and the beads were dried, as described in Example 6.

Example 9

Comparative Dissolution Study I

A comparative dissolution study was performed on three forms of an active ingredient: the glyburide coated beads of Example 2, a commercially available glyburide product (Micronase®, available from Pharmacia & Upjohn), and the pure glyburide bulk drug. The dissolution study was performed using a USP dissolution type 2 apparatus. For each of the three forms, material equivalent to 5 mg of glyburide was used for each triplicated dissolution run in 500 mL of isotonic pH 7.4 phosphate buffer. The dissolution medium was maintained at 37° C. and constantly stirred at a speed of 100 rpm. The dissolution media were sampled at 15, 30, 45, 60, 120 and 180 minutes. At each time point, 3 mL of the medium was sampled, and the medium was replenished with 3 mL of fresh buffer. The samples were filtered through a 0.45μ filter immediately after the sampling. The filtrates were then diluted in methanol to an appropriate concentration for a glyburide-specific HPLC assay.

The HPLC assay was performed on a Varian 9010 system by injecting 50 μL of the sample. The sample was separated on a Phenominex C18 column by running a mobile phase of 75:25 v/v methanol/phosphate buffer (0.1 M potassium dihydrogen phosphate, pH adjusted to 3.5 using phosphoric acid), at a flow rate of 1 mL/min, at ambient temperature. Glyburide was detected by its UV absorption at 229 nm.

The results of the comparative dissolution measurement were expressed as the percent of glyburide dissolved/released in the dissolution medium at a given time, relative to the initial total glyburide content present in the dissolution medium (5 mg/500 mL). The results are shown in FIG. 1, with the error bars representing the standard deviation. As the Figure shows, the glyburide coated beads of the present invention showed a superior dissolution profile in the rate, the extent, and the variability of glyburide dissolved/released into the dissolution medium, compared to the commercial Micronase® and the pure bulk drug.

Example 10

Comparative Dissolution Study II

A comparative dissolution study was performed on three forms of an active ingredient: the progesterone coated beads of Example 3, the seal coated, progesterone coated beads of Example 6, and the pure progesterone bulk drug. The dissolution study was performed using a USP dissolution type 2 apparatus. For each of the three forms, material equivalent to 100 mg of progesterone was used for each duplicated dissolution run in 900 mL of isotonic pH 7.4 phosphate buffer containing 0.5% w/v of Tween 80. The dissolution medium was maintained at 37° C. and constantly stirred at a speed of 100 rpm. The dissolution media were sampled at 30, 60, 120 and 180 minutes. At each time point, 3 mL of the medium was sampled, and the medium was replenished with 3 mL of fresh buffer/Tween solution. The samples were filtered through a 0.45μ filter immediately after the sampling. The filtrates were then diluted in methanol to an appropriate concentration for a progesterone-specific HPLC assay.

The HPLC assay was performed on a Varian 9010 system by injecting 50 μL of the sample. The sample was separated on a Phenominex C18 column by running a mobile phase of 75:25 v/v methanol/phosphate buffer (0.1 M potassium dihydrogen phosphate, pH adjusted to 3.5 using phosphoric acid), at a flow rate of 1 mL/min, at ambient temperature. Glyburide was detected by its UV absorption at 229 nm.

Figure 2A:
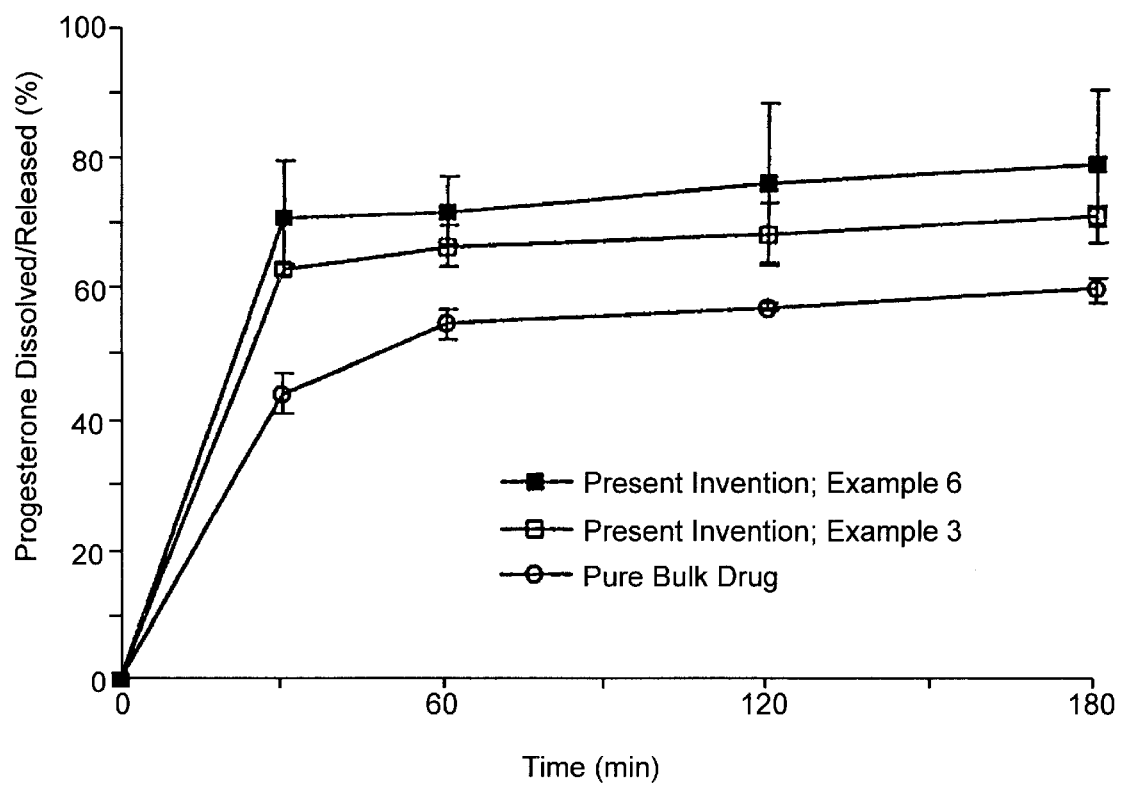
FIG. 2A is a graph showing the extent of dissolution/release of progesterone as a function of time for two compositions according to the present invention and the pure bulk drug.

The results of the comparative dissolution measurement were expressed as the percent of progesterone dissolved/released in the dissolution medium at a given time, relative to the initial total progesterone content present in the dissolution medium (100 mg/900 mL). The results are shown in FIG. 2A. As the Figure shows, the progesterone coated beads of the present invention, with or without a seal coating, showed superior dissolution profiles in both the rate and the extent of progesterone dissolved/released into the dissolution medium, compared to the pure bulk drug.

Example 11

Comparative Dissolution Study III

A comparative dissolution study was performed on three forms of an active ingredient: the progesterone coated beads of Example 3, the seal coated, progesterone coated beads of Example 6, and the pure progesterone bulk drug. Prometrium® is a capsule dosage form in which micronized progesterone is suspended in a blend of vegetable oils. The dissolution of the Prometrium® capsule was performed using a USP dissolution type 1 apparatus, and the dissolution of the other samples was performed using a USP dissolution type 2 apparatus. For each of the three forms, material equivalent to 100 mg of progesterone was used for each dissolution run in 900 mL of isotonic pH 7.4 phosphate buffer. The dissolution medium was maintained at 37° C. and constantly stirred at a speed of 100 rpm. The dissolution media were sampled at 15, 30, 45, 60 and 180 minutes. At each time point, 3 mL of the medium was sampled, and the medium was replenished with 3 mL of fresh buffer/Tween solution. The samples were filtered through a 0.45μ filter immediately after the sampling. The filtrates were then diluted in methanol to an appropriate concentration for a progesterone-specific HPLC assay.

The HPLC assay was performed on a Varian 9010 system by injecting 50 μL of the sample. The sample was separated on a Phenominex C18 column by running a mobile phase of 75:25 v/v methanol/phosphate buffer (0.1 M potassium dihydrogen phosphate, pH adjusted to 3.5 using phosphoric acid), at a flow rate of 1 mL/min, at ambient temperature. Glyburide was detected by its UV absorption at 229 nm.

Figure 2B:
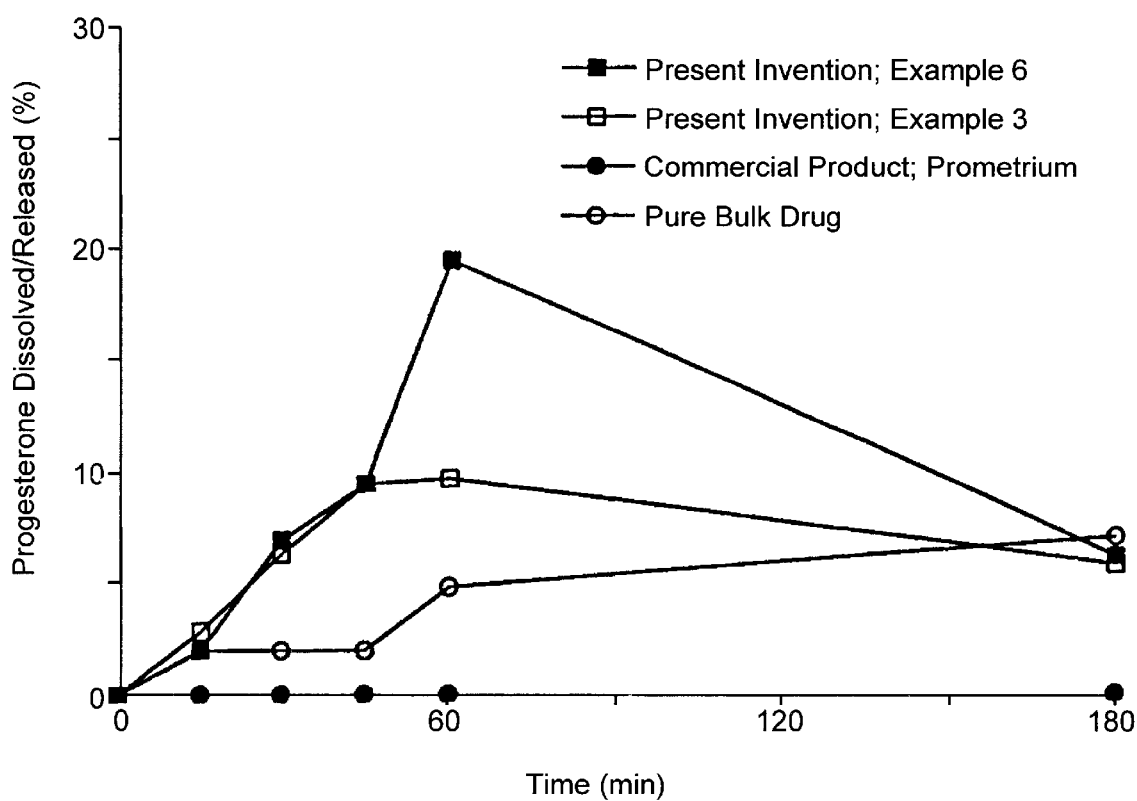
FIG. 2B is a graph showing the extent of dissolution/release of progesterone as a function of time for two compositions of the present invention, a conventional commercial formulation of progesterone, and the pure bulk drug.

The results of the comparative dissolution measurement were expressed as the percent of progesterone dissolved/released in the dissolution medium at a given time, relative to the initial total progesterone content present in the dissolution medium (100 mg/900 mL). The results are shown in FIG. 2B. As the Figure shows, the progesterone coated beads of the present invention, with or without a seal coating, showed superior dissolution profiles in both the rate and the extent of progesterone dissolved/released into the dissolution medium, compared to the commercial Prometrium® and the pure bulk drug.

Example 12

Comparative Dissolution Study IV

A comparative dissolution study was performed comparing the rate and extent of dissolution of the protective coated, omeprazole coated beads of Example 7, the enteric coated, omeprazole coated beads of Example 8 and a commercially available omeprazole product (Prilosec®, available from Astra Zeneca). The dissolution study was performed using a USP dissolution type 2 apparatus. For each of the three dosage forms, material equivalent to 5 mg of omeprazole was used for each dissolution run in 500 mL of isotonic pH 7.4 phosphate buffer. The dissolution medium was maintained at 37° C. and constantly stirred at a speed of 100 rpm. The dissolution media were sampled at 15, 30, 45 and 60 minutes. At each time point, 3 mL of the medium was sampled, and the medium was replenished with 3 mL of fresh buffer. The samples were filtered through a 0.45μ filter immediately after the sampling. The filtrates were then diluted in methanol to an appropriate concentration for an omeprazole-specific HPLC assay.

The HPLC assay was performed on a Varian 9010 system by injecting 50 μL of the sample. The sample was separated on a Phenominex C18 column by running a mobile phase of 30:70 v/v acetonitrile/phosphate buffer (pH 7.4), at a flow rate of 1.1 mL/min, at ambient temperature. Omeprazole was detected by its UV absorption at 302 nm.

Figure 3:
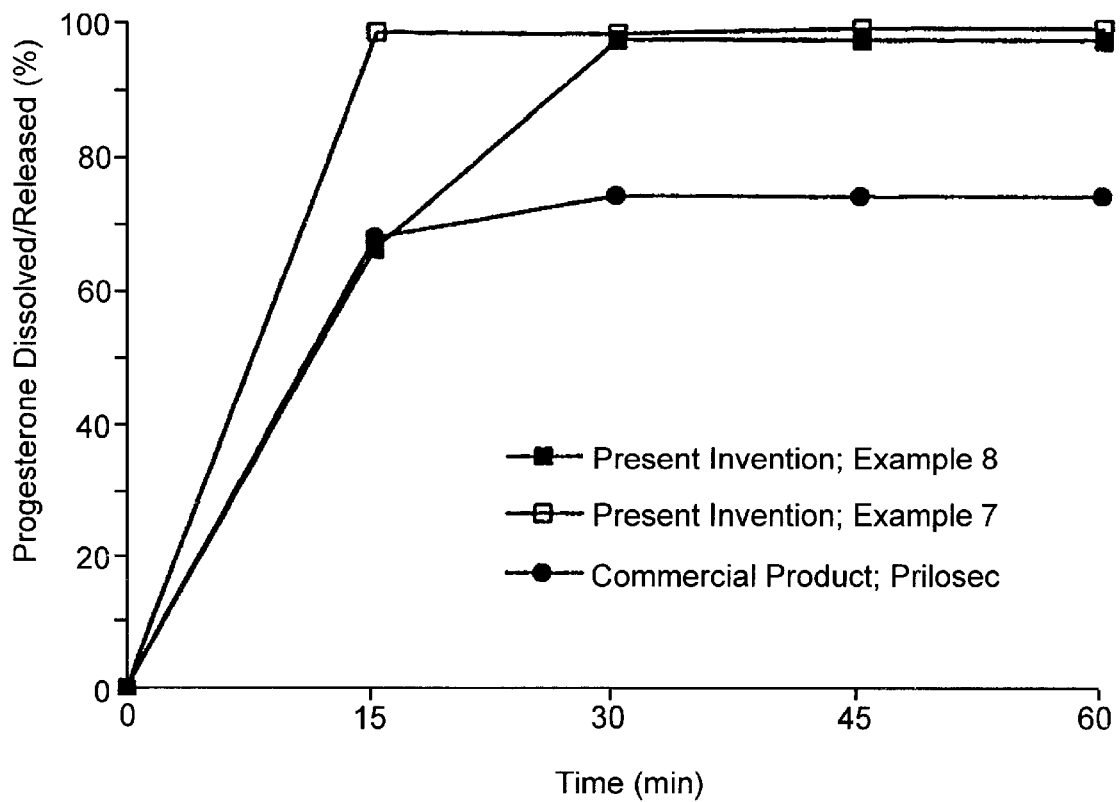
FIG. 3 is a graph showing the extent of dissolution/release of omeprazole as a function of time for two compositions according to the present invention and a prior art composition.

The results of the comparative dissolution measurement were expressed as the percent of omeprazole dissolved in the dissolution medium at a given time, relative to the initial total omeprazole content present in the dissolution medium (5 mg/500 mL). The results are shown in FIG. 3. As the Figure shows, the omeprazole coated beads of the present invention showed superior dissolution profiles in both the rate and the extent of omeprazole dissolved/released into the dissolution medium, compared to the commercial Prilose® product.

The following non-limiting examples 13–28 illustrate compositions that can be prepared according to the present invention. It should be appreciated that the compositions can be prepared in the absence of the active ingredients and appropriate amounts of the active ingredients in any given dosage form then can be administered together or separately with the composition. It should also be appreciated that the compositions can further include additional additives, excipients, and other components for the purpose of facilitating the processes involving the preparation of the composition or the pharmaceutical dosage form, as described herein, as is well-known to those skilled in the art.

Example 13

| Component | Amount (g) |
| --- | --- |
| Atorvastatin | 4 |
| Partially hydrogenated soybean oil | 10 |
| Myrj 52 (PEG-40 stearate) | 70 |
| Monomuls 90-45 (glyceryl monolaurate) | 20 |
| Non-pareil seed (25/30 mesh) | 120 |

Example 14

| Component | Amount (g) |
| --- | --- |
| Alendronate sodium | 50 |
| Cremophor PH-40 (PEG-40 hydrogenated castor oil) | 100 |
| Capmul MCM (glyceryl caprylate/caprate) | 50 |
| Sodium alginate | 2 |
| Water | 5 |
| Non-pareil seed (25/30 mesh) | 200 |

Example 15

| Component | Amount (g) |
| --- | --- |
| Ganciclovir | 100 |
| Tocopheryl PEG-1000 succinate | 200 |

-continued

| Component | Amount (g) |
| --- | --- |
| Imwitor 191 (glyceryl monostearate) | 30 |
| Water | 20 |
| Non-pareil seed (25/30 mesh) | 400 |

Example 16

| Component | Amount (g) |
| --- | --- |
| Simvastatin | 20 |
| Hydrogenated castor oil | 40 |
| Crodet O40 (PEG-40 oleate) | 200 |

Example 17

| Component | Amount (g) |
| --- | --- |
| Zafirlukast | 7 |
| PEG-150 monostearate | 50 |
| PEG-40 monostearate | 80 |
| Peceol (glyceryl monooleate) | 15 |

Example 18

| Component | Amount |
| --- | --- |
| Salmon calcitonin | 300,000 IU |
| PEG-40 monostearate | 200 g |
| Glycerol monolaurate | 100 g |
| Water | 5 g |

Example 19

| Component | Amount (g) |
| --- | --- |
| Lovastatin | 20 |
| Coenzyme Q10 | 50 |
| PEG-40 stearate | 150 |
| Glycerol monolaurate | 50 |
| Non-pareil seed (25/30 mesh) | 200 |

Example 20

| Component | Amount (g) |
| --- | --- |
| Tacrolimus | 5 |
| Solulan C-24 | 130 |
| Distilled monoglycerides | 40 |
| Deoxycholic acid | 80 |
| Non-pareil seed (35/40 mesh) | 250 |

Example 21

| Component | Amount (g) |
| --- | --- |
| Rapamycin | 20 |
| PEG-40 stearate | 150 |
| PEG-150 stearate | 50 |
| Miglyol 812 | 20 |

Example 22

| Component | Amount (g) |
| --- | --- |
| Pioglitazone | 15 |
| Pureco 76 | 20 |
| Lutrol OP 2000 | 30 |
| PEG-100 hydrogenated castor oil | 100 |
| PEG-100 oleate (Crodet O-100) | 100 |
| Non-pareil seed (25/30 mesh) | 200 |

Example 23

| Component | Amount (g) |
| --- | --- |
| Oxaprozin | 50 |
| Safflower oil | 25 |
| PEG-10 soya sterol (Nikkol BYS-20) | 25 |
| Myrj 52 | 150 |
| Non-pareil seed (25/30 mesh) | 300 |

Example 24

| Component | Amount (g) |
| --- | --- |
| Tretinoin | 50 |
| Capmul GMO-K | 50 |
| Sodium taurocholate | 100 |
| DPPC | 50 |
| DMPC | 50 |

Example 25

| Component | Amount (g) |
| --- | --- |
| Celecoxib | 50 |
| Myrj 52 | 100 |
| Glycerol monolaurate | 30 |
| Hydrogenated coconut oil | 20 |
| Non-pareil seed (25/30 mesh) | 200 |

Example 26

| Component | Amount (g) |
| --- | --- |
| Rofecoxib | 10 |
| Kessco PEG 1540 MS (PEG-32 stearate) | 160 |
| Imwitor 312 | 20 |
| Hydrogenated palm oil (Softisan 154) | 20 |

Example 27

| Component | Amount (g) |
| --- | --- |
| Fenofibrate | 100 |
| Imwitor 742 | 40 |
| Imwitor 988 | 40 |
| Sodium alginate | 4 |
| Crodet O-40 | 120 |
| Myrj 51 | 120 |
| Water | 20 |

Example 28

| Component | Amount (g) |
| --- | --- |
| Saquinavir | 200 |
| HPMC | 50 |
| Myrj 52 | 130 |
| Arlacel 186 | 20 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A pharmaceutical composition in the form of a solid carrier comprising a substrate and an encapsulation coat on the substrate, wherein the encapsulation coat comprises an admixture of a therapeutically effective amount of a hydrophobic pharmaceutical active ingredient, an effective solubilizing amount of at least one hydrophilic surfactant, and a lipophilic additive selected from the group consisting of lipophilic surfactants, triglycerides, and combinations thereof, wherein the effective solubilizing amount of the at least one hydrophilic surfactant is an amount effective to partially or fully solubilize the pharmaceutical active ingredient in the encapsulation coat.

2. The pharmaceutical composition of claim 1, wherein the active ingredient is a drug, a nutrient, a cosmeceutical, a diagnostic agent, a salt thereof, an isomer thereof, a derivative thereof, or a mixture thereof.

3. The pharmaceutical composition of claim 1, wherein the hydrophobic active ingredient has an intrinsic aqueous solubility of less than about 1 mg/mL.

4. The pharmaceutical composition of claim 3, wherein the active ingredient is selected from the group consisting of analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastroin-testinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

5. The pharmaceutical composition of claim 3, wherein the active ingredient is selected from the group consisting of acetretin, albendazole, albuterol, aminoglutethimide, aminodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptotliecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporine, danazol, dantrolene, dexchlorpheniramine, diclofenac, dicoumarol, digoxin, dehydroepiandrosterone, dihydroergotamine, dihydrotachysterol, dirithromycin, donezepil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griscofulvin, halofantrine, ibuprofen, irbesartan, irinotecan, isosorbide dinitrate, isotretinoin, itraconazole, ivermectin, ketoconazole, ketorolac, lamotrigine, lanosprazole, leflunomide, lisinopril, loperamide, loratadine, lovastatin, L-thyroxine, lutein, lycopene, medroxyprogesterone, mifepristone, mefloquine, megestrol acetate, methadone, methoxsalen, metronidazole, miconazolo, midazolam, miglitol, minoxidil, mitoxantrone, montelukast, nabumetone, nalbuphine, nelfinavir, nifedipine, nilsolidipine, nilutanide, nitrofurantoin, nizatidine, omeprazole, oprevelkin, ocstradiol, oxaprozin, paclitaxel, paracalcitol, paroxetine, pentazocine, pioglitazone, pizofelin, pravastatin, prednisolone, probucol, progesterone, pseudoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacroliinus, tamoxifen, tamsulosin, targretin, tazarotene, telmisartan, teniposide, terbinafine, terazosin, tetrahydrocannabinol, tiagabine, ticlopidine, tirofibran, tizanidine, topirmate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

6. The pharamaeutical composition of claim 3, wherein the active ingredient is selected from the group consisting of acetretin, albendazole, albuterol, aminoglutethimide, amiodarone, amlodipine, amphetamine, amphotericin B, atorvastatin, atovaquone, azithromycin, baclofen, benzonatate, bicalutanide, busulfan, butenafine, calcifediol, calcipotriene, calcitriol, camptothecin, capsaicin, carbamezepine, carotenes, celecoxib, cerivastatin, chlorpheniramine, cholecaliferol, cimetidine, cinnarizine, ciprofloxacin, cisapride, cetirizine, clarithromycin, clemastine, clomiphene, codeine, coenzyme Q10, cyclosporine, danazol, dantrolene, dexchlorpheniramine, diclofenac, digoxin, dehydroepiandrosterone, dihydroergotamine, dihydrotachysterol, dirithromycin, donezepil, efavirenz, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irinotecan, isotretinoin, itraconazole, ivermectin, ketoconazole, ketorolac, lamotrigine, lanosprazole, leflunomide, loperamide, loratadine, lovastatin, L-thryroxine, lutein, lycopene, mifepristone, mefloquine, megestrol acetate, methdone, methoxsalen, metronidazole, miconazole, midazolam, miglitol, mitoxantrone, medroxyprogesterone, montelukast, nabumetone, nalbuphine, naratriptan, nelfinavir, nilutanide, nitrofurantoin, nizatidine, omeprazole, oestradiol, oxaprozin, paclitaxel, paracalcitol, pentazocine, pioglitazone, pizofetin, pravastatin, probucol, progesterone, pseduoephedrine, pyridostigmine, rabeprazole, raloxifene, rofecoxib, repaglinide, rifabutine, rifapentine, rimexolone, ritanovir, rizatriptan, rosiglitazone, saquinavir, sibutramine, sildenafil citrate, simvastatin, sirolimus, spironolactone, sumatriptan, tacrine, tacrolimus, tamoxifen, tamsulosin, targretin, tazarotene, teniposide, terbinafine, tetrahydrocannabinol, tiagabine, tizanidine, topiramate, topotecan, toremifene, tramadol, tretinoin, troglitazone, trovafloxacin, verteporfin, vigabatrin, vitamin A, vitamin D, vitamin E, vitamin K, zafirlukast, zileuton, zolmitriptan, zolpidem, zopiclone, pharmaceutically acceptable salts, isomers and derivatives thereof, and mixtures thereof.

7. The pharmaceutical composition of claim 3, wherein the active ingredient is selected from the group consisting of acetretin, albuterol, aminoglutethimide, amiodarone, amlodipine, amprenavir, atorvastatin, atovaquone, baclofen, benzonatate, bicalutanide, busulfan, calcifediol, calcipotriene, calcitriol, camptothecin, capsaicin, carbamezepine, carotenes, celecoxib, chlorpheniramine, cholecaliferol, cimetidine, cinnarizine, cisapride, citrizine, clemastine, coenzyme Q10, cyclosporin, danazol, dantrolene, dexchlorpheniramine, diclofenac, dehydroepiandrosterone, dihydroergotamine, dihydrotachysterol, efavirenz, ergocalciferol, ergotamine, essential fatty acid sources, etodolac, etoposide, famotidine, fenofibrate, fexofenadine, finasteride, fluconazole, flurbiprofen, fosphenytoin, frovatriptan, furzolidone, glibenclamide, glipizide, glyburide, glimepiride, ibuprofen, irinotecan, isotretinoin, itraconazole, ivermectin, ketoconazole, ketorolac, lamotrigine, lansoprazole, leflunomide, loperamide, loratadine, lovastatin, L-thryroxine, lutein, lycopene, medroxyprogesterone, mifepristone, megestrol acetate, methoxsalen, metronidazole, miconazole, miglitol, mitoxantrone, montelukast, nabumetone, naratriptan, nelfinavir, nilutanide, nitrofurantoin, nizatidine, omeprazole, oestradiol, oxaprozin, paclitaxel, paracalcitol, pioglitazone, pizofetin, pranlukast, probucol, progesterone, pseduoephedrine, rabeprazole, raloxifene, rofecoxib, repaglinide, rifabutine, rifapentine, rimexolone, ritanovir, rizatriptan, rosiglitazone, saquinavir, sildenafil citrate, simvastatin, sirolimus, tacrolimus, tamoxifen, tamsulosin, targretin, tazarotene, teniposide, terbenafine, tetrahydrocannabinol, tiagabine, tizanidine, topiramate, topotecan, toremifene, tramadol, tretinoin, troglitazone, trovafloxacin, ubidecarenone, vigabatrin, vitamin A, vitamin D, vitamin E, vitamin K, zafirlukast, zileuton, zolmitriptan, pharmaceutically acceptable salts, isomers and derivative thereof, and mixtures thereof.

8. The pharmaceutical composition of claim 3, wherein the active ingredient is selected from the group consisting of amlodipine, amprenavir, atorvastatin, atovaquone, celecoxib, cisapride, coenzyme Q10, cyclosporin, famotidine, fenofibrate, fexofenadine, finasteride, ibuprofen, itraconazole, lansoprazole, loratadine, lovastatin, megestrol acetate, montelukast, nabumetone, nizatidine, omeprazole, oxaprozin, pacliaxel, paracalcitol, pioglitazone, pranlukast, progesterone, pseduoephedrine, rabeprazole, rapamycin, rofecoxib, repaglinide, rimexolone, ritanovir, rosiglitazone, saquinavir, sildenafil citrate, simvastatin, sirolimus, tacrolimus, tamsulosin, teniposide, terbenafine, tetrahydrocannabinol, tiagabine, tizanidine, tranadol, troglitazone, vitamin A, vitamin D, vitamin E, zafirlukast, zileuton, pharmaceutically acceptable salts, isomers and derivatives thereof, and mixtures thereof.

9. The pharmaceutical composition of claim 1, wherein the at least one hydrophilic surfactant comprises a non-ionic hydrophilic surfactant having an HLB value of at least about 10.

10. The pharmaceutical composition of claim 9, wherein the non-ionic hydrophilic surfactant is selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; tocopherol polyethylene glycol succinates; sugar esters; sugar ethers; sucroglycerides; and mixtures thereof.

11. The pharmaceutical composition of claim 1, wherein the at least one hydrophilic surfactant comprises an ionic surfactant.

12. The pharmaceutical composition of claim 11, wherein the ionic surfactant is selected from the group consisting of alkyl ammonium salts; bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-,diacetylated tartaric acid esters of mono-,diglycerides; succinylated monoglycerides; citric acid esters of mono-,diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; and mixtures thereof.

13. The pharmaceutical composition of claim 1, wherein the substrate is a powder or a multiparticulate.

14. The pharmaceutical composition of claim 1, wherein the substrate is an additive, an active ingredient or a mixture thereof.

15. The pharmaceutical composition of claim 14, wherein the substrate is an additive selected from the group consisting of a solubilizer, an enzyme inhibitor, an anti-adherent, an anticoagulant, an antifoaming agent, an antioxidant, a binder, a bufferant, a chelating agent, a coagulant, a colorants or opaquants, a coolant, a cryoprotectant, a diluent or filler, a disintegrant or super disintegrant, a hydrogen bonding agent, a flavorant or desensitizer, an ion-exchange resin, a plasticizer, a preservative, a solvent, a sweetener, a thickener, or mixtures thereof.

16. The pharmaceutical composition of claim 13, wherein the substrate is a multiparticulate selected from the group consisting of a granule, a pellet, a bead, a spherule, a beadlet, a microcapsule, a millisphere, a nanocapsule, a nanosphere, a microsphere, a platelet, a tablet and a capsule.

17. The pharmaceutical composition of claim 1, wherein the solid carrier is a bead, a beadlet, a granule, a spherule, a pellet, a microcapsule, a microsphere, a nanosphere, a film, a wafer, a sprinkle, an implant, a troche, a lozenge, a platelet, a nanocapsule or a strip.

18. The pharmaceutical composition of claim 1, wherein the lipophilic additive is selected from the group consisting of lipophilic surfactants.

19. The pharmaceutical composition of claim 18, wherein the lipophilic additive is selected from the group consisting of alcohols; polyoxyethylene alkylethers; fatty acids; bile acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

20. The pharmaceutical composition of claim 1, wherein the lipophilic additive is a triglyceride selected from the group consisting of vegetable oils, fish oils, animal fats, hydrogenated vegetable oils, partially hydrogenated vegetable oils, synthetic triglycerides, modified triglycerides, fractionated triglycerides, and mixtures thereof.

21. The pharmaceutical composition of claim 1, wherein the solid carrier is enteric coated, coated for fast disintegration, seal coated, film coated, barrier coated, compress coated, or coated with an enzyme-degradable coating.

22. The pharmaceutical composition of claim 1, wherein the admixture of the encapsulation coat is prepared by a process selected from agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, and spray drying.

23. The pharmaceutical composition of claim 1, in the form of a capsule, a tablet, an ovule, a suppository, a wafer, a chewable tablet, a buccal tablet, a sub lingual tablet, a quick-dissolve tablet, an effervescent tablet, a granule, a pellet, a bead, a pill, a sachet, a sprinkle, a film, a dry syrup, a reconstitutable solid, a suspension, a lozenge, a troche, an implant, a power, a triturate, a platelet, or a strip.

24. The pharmaceutical composition of claim 1, wherein the composition is formulated for immediate release, pulsatile release, controlled release, extended release, delayed release, targeted release, or targeted delayed release.

25. The pharmaceutical composition of claim 1, wherein the composition is formulated for oral, nasal, ocular, urethral, buccal, transmucosal, vaginal, topical or rectal delivery.

26. A method of administering an active ingredient to a mammal, the method comprising administering to the mammal a dosage form of the pharmaceutical composition of claim 1.

27. The method of claim 26, wherein the mammal is a human.

28. The pharmaceutical composition of claim 1, wherein the weight ratio of lipophilic additive to the at least one hydrophilic surfactant is in the range of approximately 0.10:1 to approximately 0.92:1.

29. A pharmaceutical composition in the form of a solid carrier comprising an admixture of a hydrophobic pharmaceutical active ingredient an effective solubilizing amount of at least one hydrophilic surfactant, and a lipophilic additive selected from the group consisting of lipophilic surfactants, triglycerides, and combinations thereof, wherein the effective solubilizing amount of the at least one hydrophilic surfactant is an amount effective to partially or fully solubilize the pharmaceutical active ingredient in the solid carrier.

30. The pharmaceutical composition of claim 29, wherein the weight ratio of lipophilic additive to the at least one hydrophilic surfactant is in the range of approximately 0.10:1 to approximately 0.92:1.

31. The pharmaceutical composition of claim 29, wherein the active ingredient is a drug, a nutrient, a cosmeceutical, a diagnostic agent, a salt thereof, an isomer thereof, a derivative thereof, or a mixture thereof.

32. The pharmaceutical composition of claim 29, wherein the hydrophobic active ingredient has an intrinsic aqueous solubility of less than about 1 mg/mL.

33. The pharmaceutical composition of claim 31, wherein the active ingredient is selected from the group consisting of analgesics, anti-inflammatory agents, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-Blockers, cardiac inotropic agents, corticosteroids, diuretics, anti-parkinsonian agents, gastro-intestinal agents, histamine receptor antagonists, keratolytics, lipid regulating agents, anti-anginal agents, cox-2 inhibitors, leucotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non-essential fatty acids, and mixtures thereof.

34. The pharmaceutical composition of claim 32, wherein the active ingredient is selected from the group consisting of acetretin, albendazole, albuterol, aminoglutethimide, amiodarone, amlodipine, amphetamine, amphotericin B, atorvastatin, atovaquone, azithromycin, baclofen, beclomethasone, benezepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicoumarol, digoxin, dehydroepiandrosterone, dihydroergotamine, dihydrotachysterol, dirithromycin, donepezil, efavirenz, eposartan, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thryroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nilsolidipine, nilutanide, nitrofurantoin, nizatidine, omeprazole, oprevelkin, oestradiol, oxaprozin, paclitaxel, paracalcitol, paroxetine, pentazocine, pioglitazone, pizofetin, pravastatin, prednisolone, probucol, progesterone, pseduoephedrine, pyridostigmine, rabeprazole, raloxifene, rofecoxib, repaglinide, rifabutine, rifapentine, rimexolone, ritanovir, rizatriptan, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabirie, ticlopidine, tirofibran, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, pharmaceutically acceptable salts, isomers, and derivatives thereof, and mixtures thereof.

35. The pharmaceutical composition of claim 32, wherein the active ingredient is selected from the group consisting of acetretin, albendazole, albuterol, aminoglutethimide, amiodarone, amlodipine, amphetamine, amphotericin B, atorvastatin, atovaquone, azithromycin, baclofen, benzonatate, bicalutanide, busulfan, butenafine, calcifediol, calcipotriene, calcitriol, camptothecin, capsaicin, carbamezepine, carotenes, celecoxib, cerivastatin, chlorpheniramine, cholecaliferol, cimetidine, cinnarizine, ciprofloxacin, cisapride, cetirizine, clarithromycin, clemastine, clomiphene, codeine, coenzyme Q10, cyclosporin, danazol, dantrolene, dexchlorpheniramine, diclofenac, digoxin, dehydrepiandrosterone, dihydroergotamine, dihydrotachysterol, dirithromycin, donepezil, efavirenz, ergocalciferol, ergotamine, essential fatty acid sources, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irinotecan, isotretinoin, itraconazole, ivermectin, ketoconazole, ketorolac, lamotrigine, lansoprazole, leflunomide, loperamide, loratadine, lovastatin, L-thryroxine, lutein, lycopene, mifepristone, mefloquine, megestrol acetate, methdone, methoxsalen, metronidazole, miconazole, midazolam, miglitol, mitoxantrone, medroxyprogesterone, montelukast, nabumetone, nalbuphine, naratriptan, nelfinavir, nilutanide, nitrofurantoin, nizatidine, omeprazole, oestradiol, oxaprozin, paclitaxel, paracalcitol, pentazocine, pioglitazone, pizofetin, pravastatin, probucol, progesterone, pseduoephedrine, pyridostigmine, rabeprazole, raloxifene, rofecoxib, repaglinide, rifabutine, rifapentine, rimexolone, ritanovir, rizatriptan, rosiglitazone, saquinavir, sibutramine, sildenafil citrate, simvastatin, sirolimus, spironolactone, sumatriptan, tacrine, tacrolimus, tamoxifen, tamsulosin, targretin, tazarotene, teniposide, terbinafine, tetrahydrocannabinol, tiagabine, tizanidine, topiramate, topotecan, toremifene, tramadol, tretinoin, troglitazone, trovafloxacin, verteporfin, vigabatrin, vitamin A, vitamin D, vitamin E, vitamin K, zafirlukast, zileuton, zolmitriptan, zolpidem, zopiclone, pharmaceutically acceptable salts, isomers and derivatives thereof, and mixtures thereof.

36. The pharmaceutical composition of claim 32, wherein the active ingredient is selected from the group consisting of acetretin, albuterol, aminoglutethimide, amiodarone, amlodipine, amprenavir, atorvastatin, atovaquone, baclofen, benzonatate, bicalutanide, busulfan, calcifediol, calcipotriene, calcitriol, camptothecin, capsaicin, carbamezepine, carotenes, celecoxib, chlorpheniramine, cholecaliferol, cimetidine, cinnarizine, cisapride, citrizine, clemastine, coenzyme Q10, cyclosporin, danazol, dantrolene, dexchlorpheniramine, diclofenac, dehydroepiandrosterone, dihydroergotamine, dihydrotachysterol, efavirenz, ergocalciferol, ergotamine, essential fatty acid sources, etodolac, etoposide, famotidine, fenofibrate, fexofenadine, finasteride, fluconazole, flurbiprofen, fosphenytoin, frovatriptan, furzolidone, glibenclamide, glipizide, glyburide, glymepride, ibuprofen, irinotecan, isotretinoin, itraconazole, ivermectin, ketoconazole, ketorolac, lamotrigine, lansoprazole, leflunomide, loperamide, loratadine, lovastatin, L-thryroxine, lutein, lycopene, medroxyprogesterone, mifepristone, megestrol acetate, methoxsalen, metronidazole, miconazole, miglitol, mitoxantrone, montelukast, nabumetone, naratriptan, nelfinavir, nilutanide, nitrofurantoin, nizatidine, omeprazole, oestradiol, oxaprozin, paclitaxel, paracalcitol, pioglitazone, pizofetin, pranlukast, probucol, progesterone, pseudoephedrine, rabeprazole, raloxifene, rofecoxib, repaglinide, rifabutine, rifapentine, rimexolone, ritanovir, rizatriptan, rosiglitazone, saquinavir, sildenafil citrate, simvastatin, sirolimus, tacrolimus, tamoxifen, tamsulosin, targretin, tazarotene, teniposide, terbenafine, tetrahydrocannabinol, tiagabine, tizanidine, topiramate, topotecan, toremifene, tramadol, tretinoin, troglitazone, trovafloxacin, ubidecarenone, vigabatrin, vitamin A, vitamin D, vitamin E, vitamin K, zafirlukast, zileuton, zolmitriptan, pharmaceutically acceptable salts, isomers and derivative thereof, and mixtures thereof.

37. The pharmaceutical composition of claim 32, wherein the active ingredient is selected from the group consisting of amlodipine, amprenavir, atorvastatin, atovaquone, celecoxib, cisapride, coenzyme Q10, cyclosporin, famotidine, fenofibrate, fexofenadine, finasteride, ibuprofen, itraconazole, lansoprazole, loratadine, lovastatin, megestrol acetate, montelukast, nabumetone, nizatidine, omeprazole, oxaprozin, paclitaxel, paracalcitol, pioglitazone, pranlukast, progesterone, pseudoephedrine, rabeprazole, rapamycin, rofecoxib, repaglinide, rimexolone, ritanovir, rosiglitazone, saquinavir, sildenafil citrate, simvastatin, sirolimus, tacrolimus, tamsulosin, teniposide, terbenafine, tetrahydrocannabinol, tiagabine, tizanidine, tramadol, troglitazone, vitamin A, vitamin D, vitamin E, zafirlukast, zileuton, pharmaceutically acceptable salts, isomers and derivatives thereof, and mixtures thereof.

38. The pharmaceutical composition of claim 29, wherein the at least one hydrophilic surfactant comprises a non-ionic hydrophilic surfactant having an HLB value of at least about 10.

39. The pharmaceutical composition of claim 38, wherein the non-ionic hydrophilic surfactant is selected from the group consisting of alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; tocopherol polyethylene glycol succinates; sugar esters; sugar ethers; sucroglycerides; and mixtures thereof.

40. The pharmaceutical composition of claim 29, wherein the at least one hydrophilic surfactant comprises an ionic surfactant.

41. The pharmaceutical composition of claim 40, wherein the ionic surfactant is selected from the group consisting of alkyl ammonium salts; bile acids and salts, analogues, and derivatives thereof; fatty acid derivatives of amino acids, carnitines, oligopeptides, and polypeptides; glyceride derivatives of amino acids, oligopeptides, and polypeptides; acyl lactylates; mono-,diacetylated tartaric acid esters of mono-,diglycerides; succinylated monoglycerides; citric acid esters of mono-,diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates: salts of fatty acids; sodium docusate; and mixtures thereof.

42. The pharmaceutical composition of claim 29, wherein the solid carrier is a bead, a beadlet, a granule, a spherule, a pellet, a microcapsule, a microsphere, a nanosphere, a film, a wafer, a sprinkle, an implant, a troche, a lozenge, a platelet, a nanocapsule or a strip.

43. The pharmaceutical composition of claim 29, which further comprises a solubilizer, an enzyme inhibitor, an anti-adherent, an anticoagulant, an antifoaming agent, an antioxidant, a binder, a bufferant, a chelating agent, a coagulant, a colorants or opaquants, a coolant, a cryoprotectant, a diluent or filler, a disintegrant or super disintegrant, a hydrogen bonding agent, a flavorant or desensitizer, an ion-exchange resin, a plasticizer, a preservative, a solvent, a sweetener, a thickener, or a mixture thereof.

44. The pharmaceutical composition of claim 29, wherein the lipophilic additive is selected from the group consisting of lipophilic surfactants.

45. The pharmaceutical composition of claim 44, wherein the lipophilic additive is selected from the group consisting of alcohols; polyoxyethylene alkylethers; fatty acids; bile acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

46. The pharmaceutical composition of claim 29, wherein the lipophilic additive is a triglyceride selected from the group consisting of vegetable oils, fish oils, animal fats, hydrogenated vegetable oils, partially hydrogenated vegetable oils, synthetic triglycerides, modified triglycerides, fractionated triglycerides, and mixtures thereof.

47. The pharmaceutical composition of claim 29, wherein the solid carrier is enteric coated, coated for fast disintegration, seal coated, film coated, barrier coated, compress coated, or coated with an enzyme-degradable coating.

48. The pharmaceutical composition of claim 29, wherein the composition is processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, and spray drying.

49. The pharmaceutical composition of claim 29 in the form of a capsule, a tablet, an ovule, a suppository, a wafer, a chewable tablet, a buccal tablet, a sub-lingual tablet, a quick-dissolve tablet, an effervescent tablet, a granule, a pellet, a bead, a pill, a sachet, a sprinkle, a film, a dry syrup, a reconstitutable solid, a suspension, a lozenge, a troche, an implant, a powder, a triturate, a platelet, or a strip.

50. The pharmaceutical composition of claim 29, wherein the composition is formulated for immediate release, pulsatile release, controlled release, extended release, delayed release, targeted release, or targeted delayed release.

51. The pharmaceutical composition of claim 29, wherein the composition is formulated for oral, nasal, ocular, urethral, buccal, transmucosal, vaginal, topical or rectal delivery.

52. A method of administering an active ingredient to a mammal, the method comprising administering to the mammal a dosage form of the pharmaceutical composition of claim 29.

53. The method of claim 52, wherein the mammal is a human.

54. The pharmaceutical composition of claim 22, wherein the admixture of the encapsulation coat is prepared by a process selected from air suspension chilling, air suspension drying, compression, cryopelletization, encapsulation, extrusion, lyophilization, molding, spheronization, spray chilling, spray congealing, and spray drying.

55. The pharmaceutical composition of claim 48, wherein the admixture of the encapsulation coat is prepared by a process selected from air suspension chilling, air suspension drying, compression, cryopelletization, encapsulation, extrusion, lyophilization, molding, spheronization, spray chilling, spray congealing, and spray drying.

* * * * *